US012642536B2

(12) United States Patent
Otto et al.

(10) Patent No.: US 12,642,536 B2
(45) Date of Patent: **\*Jun. 2, 2026**

(54) SURGICAL ROBOTICS SYSTEM WITH MODE SWITCHING

(71) Applicant: MAKO Surgical Corp., Weston, FL (US)

(72) Inventors: Jason Otto, Plantation, FL (US); Radu Iorgulescu, Weston, FL (US); Chris Lightcap, Davie, FL (US); Brian Schmitz, Fort Lauderdale, FL (US); Jason Wojcik, Weston, FL (US); Carinne Cecile Granchi, Weston, FL (US)

(73) Assignee: MAKO SURGICAL CORP., Weston, FL (US)

( \* ) Notice: Subject to any disclaimer, the term of this patent is extended or adjusted under 35 U.S.C. 154(b) by 29 days.

This patent is subject to a terminal disclaimer.

(21) Appl. No.: 18/914,732

(22) Filed: Oct. 14, 2024

(65) Prior Publication Data

US 2025/0032126 A1 Jan. 30, 2025

Related U.S. Application Data

(63) Continuation of application No. 18/512,830, filed on Nov. 17, 2023, now Pat. No. 12,150,652, which is a (Continued)

(51) Int. Cl.
*A61B 34/10* (2016.01)
*A61B 17/14* (2006.01)
(Continued)

(52) U.S. Cl.
CPC ............ *A61B 17/15* (2013.01); *A61B 17/142* (2016.11); *A61B 17/1615* (2013.01);
(Continued)

(58) Field of Classification Search
CPC ..... A61B 17/142; A61B 17/15; A61B 17/157; A61B 17/1615; A61B 2034/105;
(Continued)

(56) References Cited

U.S. PATENT DOCUMENTS 5,743,918 A 4/1998 Calandruccio et al.
6,377,839 B1 4/2002 Kalfas et al.
(Continued)

FOREIGN PATENT DOCUMENTS

CN 101277657 10/2008
CN 101426446 5/2009
(Continued)

OTHER PUBLICATIONS

International Search Report and Written Opinion for PCT Application No. PCT/US2013/077154, mail date Apr. 4, 2014, 17 pages.

*Primary Examiner* — Samuel S Hanna
(74) *Attorney, Agent, or Firm* — Foley & Lardner LLP

(57) ABSTRACT

A surgical method includes operating, by a surgical robot, in a first mode, detecting a crossing of an object from a first side of a boundary to a second side of the boundary, switching, in response to the crossing of the object from the first side of the boundary to the second side of the boundary, the surgical robot from the first mode to a second mode, and operating, by the surgical robot, in the second mode.

20 Claims, 25 Drawing Sheets

Related U.S. Application Data continuation of application No. 17/580,889, filed on Jan. 21, 2022, now Pat. No. 11,857,200, which is a continuation of application No. 16/538,154, filed on Aug. 12, 2019, now Pat. No. 11,259,816, which is a continuation of application No. 13/725,348, filed on Dec. 21, 2012, now Pat. No. 10,398,449.

(51) Int. Cl.

| | |
|---|---|
| *A61B 17/15* | (2006.01) |
| *A61B 17/16* | (2006.01) |
| *A61B 17/17* | (2006.01) |
| *A61B 34/00* | (2016.01) |
| *A61B 34/20* | (2016.01) |
| *A61B 34/30* | (2016.01) |
| *A61B 17/00* | (2006.01) |
| *A61B 90/00* | (2016.01) |

(52) U.S. Cl.
CPC .......... *A61B 17/1703* (2013.01); *A61B 34/20* (2016.02); *A61B 34/30* (2016.02); *A61B 34/76* (2016.02); *A61B 2017/00128* (2013.01); *A61B 17/157* (2013.01); *A61B 2034/105* (2016.02); *A61B 2034/2055* (2016.02); *A61B 34/25* (2016.02); *A61B 90/03* (2016.02)

(58) Field of Classification Search
CPC ...... A61B 17/1703; A61B 2017/00128; A61B 2034/2055; A61B 34/20; A61B 34/25; A61B 34/30; A61B 34/76; A61B 90/03
See application file for complete search history.

(56) References Cited

U.S. PATENT DOCUMENTS

| | | | |
|---|---|---|---|
| 7,842,092 | B2 | 11/2010 | Otto et al. |
| 8,475,535 | B2 | 7/2013 | Otto |
| 8,681,095 | B2 | 3/2014 | Ogawa et al. |
| 2004/0106916 | A1 | 6/2004 | Quaid et al. |
| 2004/0128026 | A1 | 7/2004 | Harris et al. |
| 2006/0142657 | A1 | 6/2006 | Quaid et al. |
| 2007/0270685 | A1 | 11/2007 | Kang et al. |
| 2008/0010706 | A1 | 1/2008 | Moses et al. |
| 2009/0306499 | A1 | 12/2009 | Van Vorhis et al. |
| 2010/0094429 | A1 | 4/2010 | Otto |
| 2010/0153076 | A1 | 6/2010 | Bellettre et al. |
| 2010/0217400 | A1 | 8/2010 | Nortman et al. |
| 2011/0066079 | A1 | 3/2011 | Otto et al. |
| 2011/0082462 | A1 | 4/2011 | Suarez et al. |
| 2011/0082587 | A1 | 4/2011 | Ziaei et al. |
| 2013/0006267 | A1* | 1/2013 | Odermatt ............... B25J 9/1628 |
| | | | 901/41 |
| 2013/0173010 | A1 | 7/2013 | Irwin et al. |
| 2013/0211419 | A1 | 8/2013 | Jensen |
| 2013/0317344 | A1 | 11/2013 | Borus et al. |

FOREIGN PATENT DOCUMENTS

| | | |
|---|---|---|
| CN | 102438551 | 5/2012 |
| JP | 2005-312991 A | 11/2005 |
| JP | 2005-334650 A | 12/2005 |
| JP | 2008-538184 A | 10/2008 |
| JP | 2008-541990 A | 11/2008 |
| JP | 2009-537229 A | 10/2009 |
| JP | 2010-524547 A | 7/2010 |
| JP | 2011-206180 A | 10/2011 |
| WO | WO-2006/091494 A1 | 8/2006 |
| WO | WO-2007/030173 A1 | 3/2007 |
| WO | WO-2007/136769 A2 | 11/2007 |
| WO | WO-2007/136771 A2 | 11/2007 |
| WO | WO-2012/101286 A1 | 8/2012 |
| WO | WO-2013/101671 | 7/2013 |

* cited by examiner

Fig. 8A
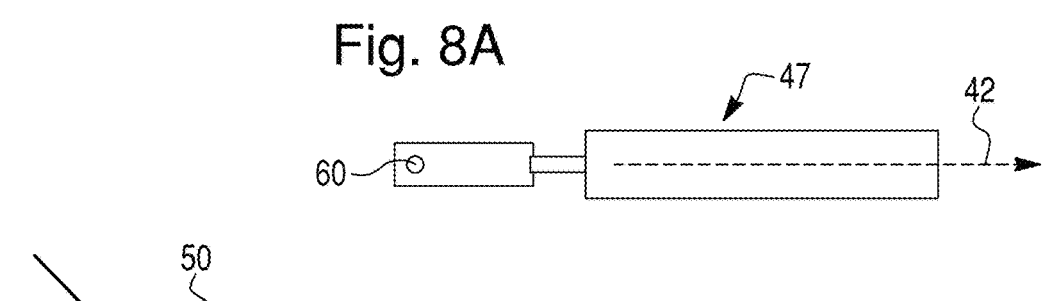
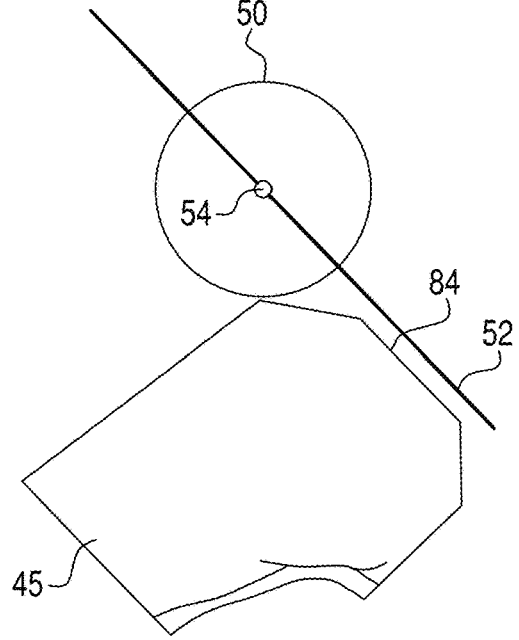
Fig. 8B

Fig. 8E

SURGICAL ROBOTICS SYSTEM WITH MODE SWITCHING

CROSS-REFERENCE TO RELATED APPLICATION

This application is a continuation of U.S. patent application Ser. No. 18/512,830, filed Nov. 17, 2023, which is a continuation of U.S. patent application Ser. No. 17/580,889, filed Jan. 21, 2022, which is a continuation of U.S. patent application Ser. No. 16/538,154, filed Aug. 12, 2019, which is a continuation of U.S. patent application Ser. No. 13/725, 348, filed Dec. 21, 2012, all of which are incorporated by reference herein in their entireties.

BACKGROUND

The present invention relates generally to the field of haptics, and more particularly to haptic control of a surgical tool.

During computer-assisted surgeries, a surgeon may utilize a haptic device. "Haptic" refers to a sense of touch, and the field of haptics relates to, among other things, human interactive devices that provide feedback to an operator. Feedback may include tactile sensations such as, for example, vibration. Feedback may also include providing force to a user, such as a positive force or a resistance to movement. A common use of haptics is to provide a user of the device with guidance or limits for manipulation of that device. For example, a haptic device may be coupled to a surgical tool, which can be manipulated by a surgeon to perform a surgical procedure. The surgeon's manipulation of the surgical tool can be guided or limited through the use of haptics to provide feedback to the surgeon during manipulation of the surgical tool.

A surgical plan is typically developed prior to performing a surgical procedure with a haptic device. The surgical plan may be patient-specific. Based on the surgical plan, the surgical system guides or limits movements of the surgical tool during portions of the surgical procedure. Control of the surgical tool serves to protect the patient and to assist the surgeon during implementation of the surgical plan.

In general, haptic devices for use during surgical procedures can have at least two modes of operation. In free mode, the surgeon can substantially freely manipulate the surgical tool coupled to the device. In haptic control mode, components of the surgical system (e.g., haptic objects) are activated to guide or limit movements of the surgical tool. Use of prior art haptic devices may be enhanced by a mechanism to improve transitions between free mode and haptic control mode during a surgical procedure.

SUMMARY

One embodiment of the invention relates to a surgical system. The surgical system includes a surgical tool associated with a virtual haptic interaction point, wherein movement of the virtual haptic interaction point corresponds to movement of the surgical tool. The surgical system further includes a processing circuit configured to establish a virtual entry boundary and activate a haptic object, wherein the activated haptic object is configured to constrain the haptic interaction point after the haptic interaction point crosses the virtual entry boundary.

Another embodiment of the invention relates to a method for using a surgical system. The method includes providing a surgical tool and providing a virtual haptic interaction point, wherein movement of the virtual haptic interaction point corresponds to movement of the surgical tool. The method further includes providing a virtual entry boundary and activating a haptic object, wherein the activated haptic object is configured to constrain the haptic interaction point after the haptic interaction point crosses the virtual entry boundary.

A still further embodiment of the invention relates to a computer-readable storage medium having instructions thereon that, when executed by a processing circuit, aid in the planning or performance of a surgical procedure. The medium includes instructions for associating a surgical tool with a virtual haptic interaction point such that movement of the virtual haptic interaction point corresponds to movement of the surgical tool; instructions for establishing a virtual entry boundary and a virtual exit boundary; instructions for activating a haptic object, wherein the activated haptic object is configured to constrain the surgical tool after the haptic interaction point crosses the virtual entry boundary; and instructions for deactivating the haptic object after the haptic interaction point crosses the virtual exit boundary.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, wherein like reference numerals refer to like elements, in which:

FIGS. 8A-8E illustrate entry and exit from haptic control when the tool axis is perpendicular to the haptic object, according to an exemplary embodiment.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting. For example, several illustrations depict methods related to haptic control entry and exit when performing specific surgical procedures on a patient's knee. However, the embodiments of haptic control described herein may be applied to haptic control of a surgical tool during any type of surgical procedure on any part of a patient, including a patient's shoulder, arm, elbow, hands, hips, legs, feet, neck, face, etc.

Exemplary Surgical System

Figure 1:
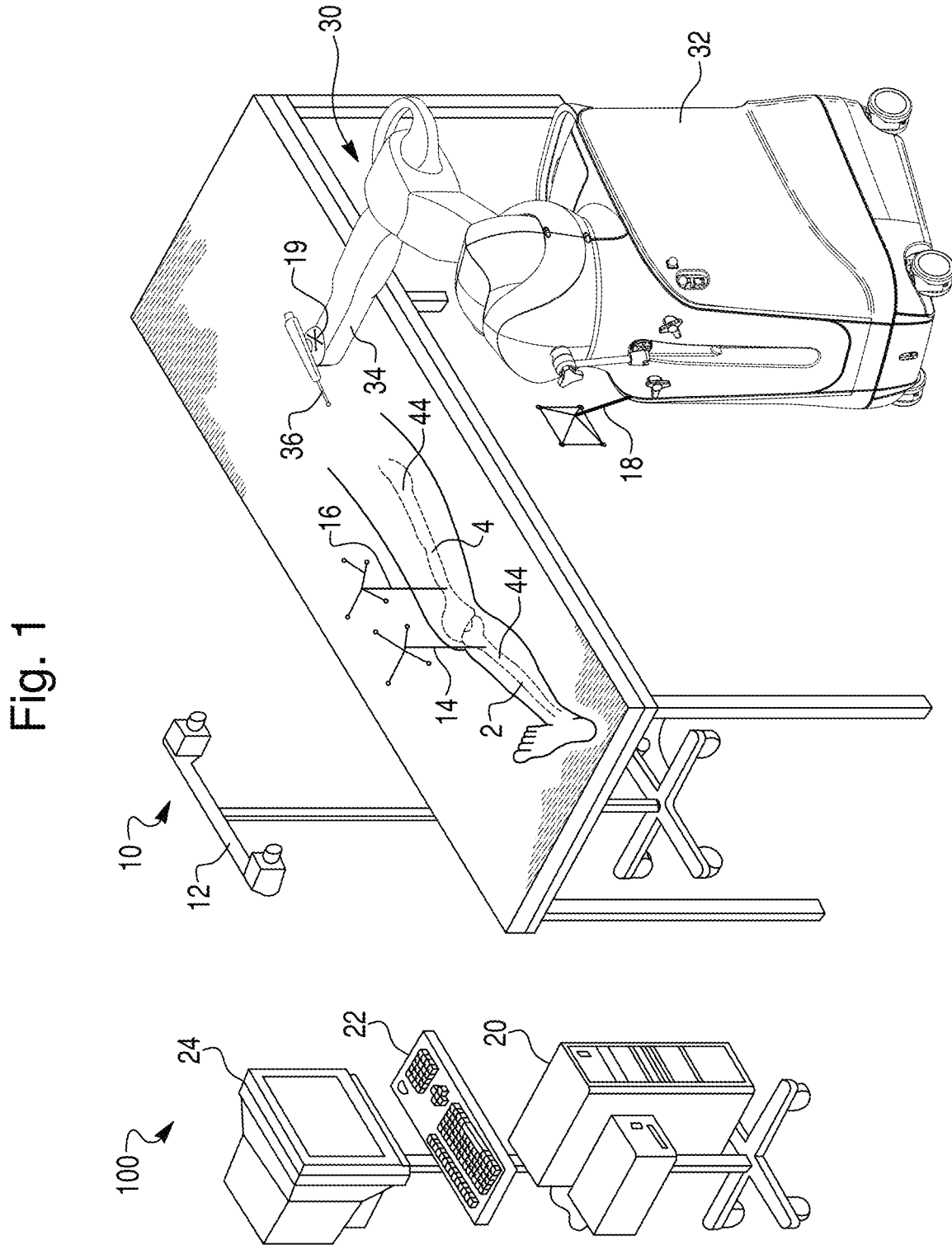
FIG. 1 is a surgical system according to an exemplary embodiment.

Referring to FIG. 1, a surgical system 100 includes a navigation system 10, a computer 20, and a haptic device 30. The navigation system tracks the patient's bone, as well as surgical tools utilized during the surgery, to allow the surgeon to visualize the bone and tools on a display 24 and to enable haptic control of a surgical tool 36 coupled to the haptic device 30.

The navigation system 10 may be any type of navigation system configured to track a patient's anatomy and surgical tools during a surgical procedure. For example, the navigation system 10 may include a non-mechanical tracking system, a mechanical tracking system, or any combination of non-mechanical and mechanical tracking systems. The navigation system 10 obtains a position and orientation (i.e. pose) of an object with respect to a coordinate frame of reference. As the object moves in the coordinate frame of reference, the navigation system tracks the pose of the object to detect movement of the object.

In one embodiment, the navigation system 10 includes a non-mechanical tracking system as shown in FIG. 1. The non-mechanical tracking system is an optical tracking system with a detection device 12 and a trackable element (e.g. navigation marker 14) that is disposed on a tracked object and is detectable by the detection device 12. In one embodiment, the detection device 12 includes a visible light-based detector, such as a MicronTracker (Claron Technology Inc., Toronto, CN), that detects a pattern (e.g., a checkerboard pattern) on a trackable element. In another embodiment, the detection device 12 includes a stereo camera pair sensitive to infrared radiation and positionable in an operating room where the surgical procedure will be performed. The trackable element is affixed to the tracked object in a secure and stable manner and includes an array of markers having a known geometric relationship to the tracked object. As is known, the trackable elements may be active (e.g., light emitting diodes or LEDs) or passive (e.g., reflective spheres, a checkerboard pattern, etc.) and have a unique geometry (e.g., a unique geometric arrangement of the markers) or, in the case of active, wired markers, a unique firing pattern.

In operation, the detection device 12 detects positions of the trackable elements, and the surgical system 100 (e.g., the detection device 12 using embedded electronics) calculates a pose of the tracked object based on the trackable elements' positions, unique geometry, and known geometric relationship to the tracked object. The navigation system 10 includes a trackable element for each object the user desires to track, such as the navigation marker 14 located on the tibia 2, navigation marker 16 located on the femur 4, haptic device marker 18 (to track a global or gross position of the haptic device 30), and an end effector marker 19 (to track a distal end of the haptic device 30).

Referring again to FIG. 1, the surgical system 100 further includes a processing circuit, represented in the figures as a computer 20. The processing circuit includes a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit and includes computer code for executing (e.g., by the processing circuit and/or processor) one or more processes described herein.

The computer 20 is configured to communicate with the navigation system 10 and the haptic device 30. Furthermore, the computer 20 may receive information related to surgical procedures and perform various functions related to performance of surgical procedures. For example, the computer 20 may have software as necessary to perform functions related to image analysis, surgical planning, registration, navigation, image guidance, and haptic guidance.

The haptic device 30 includes a base 32, a robotic arm 34, and a surgical tool 36 coupled to the robotic arm 34. The surgical tool may be any surgical tool that can be coupled to the robotic arm 34. For example, in the embodiment of FIG. 1, the surgical tool 36 is a spherical burr. The surgical tool 36 may also be a sagittal saw 38, shown in FIG. 2A, or sagittal saw 40, shown in FIG. 2B. The blade 39 of sagittal saw 38 is aligned parallel to tool axis 42, while the blade 39 of sagittal saw 40 is aligned perpendicular to tool axis 42. The surgeon can choose between a spherical burr, sagittal saw 38, sagittal saw 40, or any other type of surgical tool depending on the type of bone modification (e.g. hole, planar cut, curved edge, etc.) the surgeon desires to make.

A surgeon interacts with haptic device 30 to perform surgical procedures on a patient. In general, haptic device 30 has two modes of operation. In free mode, the surgeon can substantially freely manipulate the pose of the surgical tool 36. In haptic control mode, one or more haptic objects 52 are activated. The haptic object 52 can constrain the surgical tool 36 as described in various embodiments herein.

Development of a Surgical Plan

A surgical plan is created prior to a surgeon's performance of a surgical procedure. The surgical plan is developed utilizing a three-dimensional representation of a patient's anatomy, also referred to herein as a virtual bone model 45 (see FIGS. 3A-3D). A "virtual bone model" may include virtual representations of cartilage or other tissue in addition to bone. To obtain the virtual bone model 45, the computer 20 receives images of the patient's anatomy on which the surgical procedure is to be performed. The patient's anatomy may be scanned using any known imaging technique, such as CT, MRI, or ultrasound. The scan data is then segmented to obtain the virtual bone model 45. For example, prior to a surgical procedure on the knee, a three-dimensional representation of the femur 4 and tibia 2 is created. Alternatively, the virtual bone model 45 may be obtained by selecting a three-dimensional model from a database or library of bone models. In one embodiment, the user may use input device 22 to select an appropriate model. In another embodiment, the computer 20 may be programmed to select an appropriate model based on images or other information provided about the patient. The selected bone model(s) from the database can then be deformed based on specific patient characteristics, creating a virtual bone model 45 for use in surgical planning and implementation as described herein.

Figure 3A:
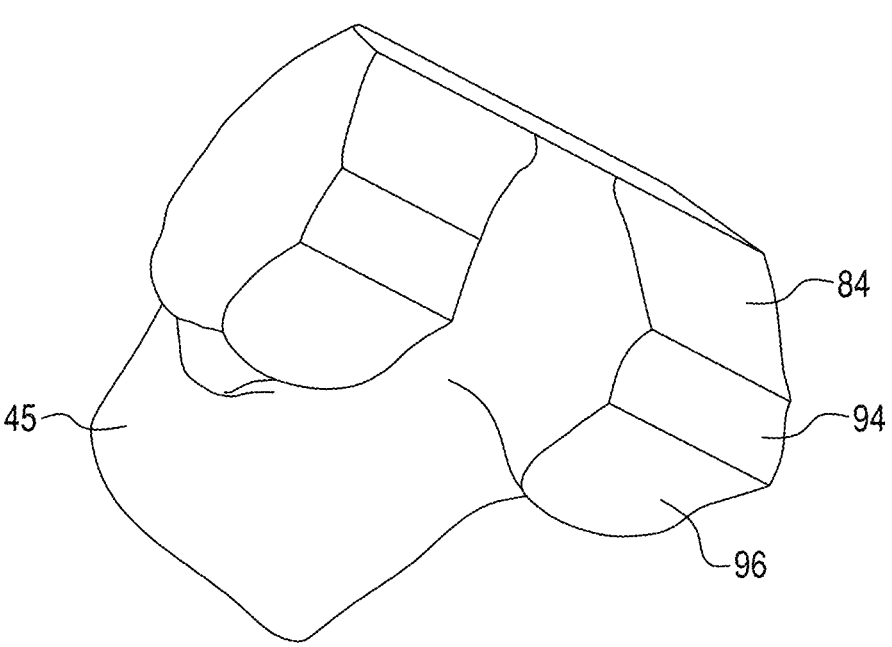
FIGS. 3A and 3B illustrate planned femur modifications according to an exemplary embodiment.
Figure 3B:
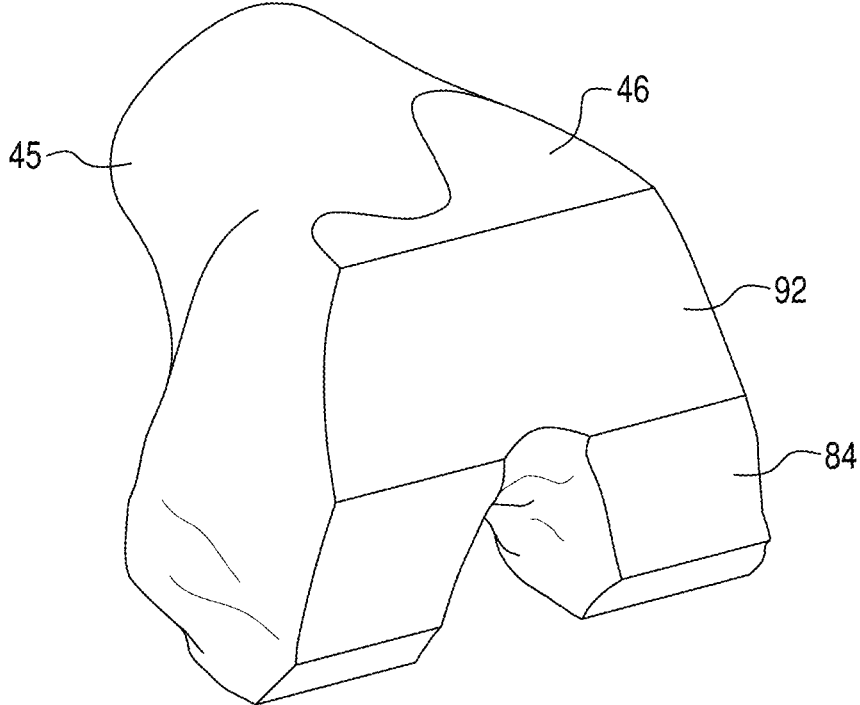
Figure 3C:
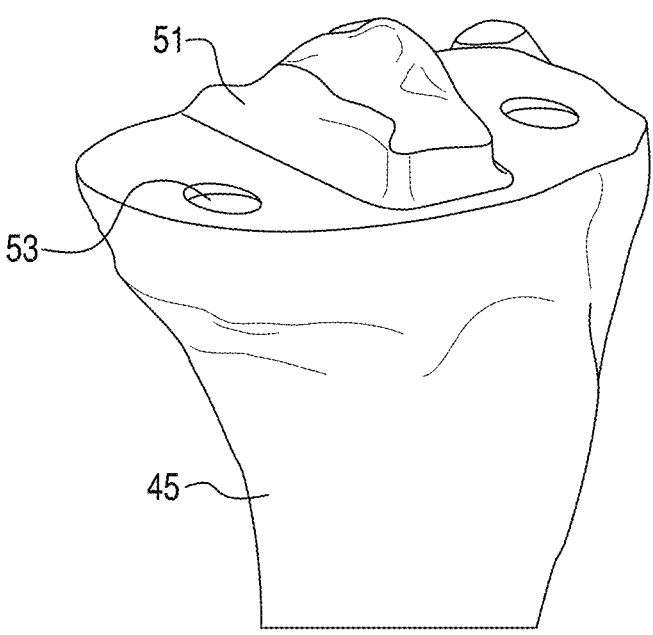
FIGS. 3C and 3D illustrate planned tibia modifications according to an exemplary embodiment.
Figure 3D:
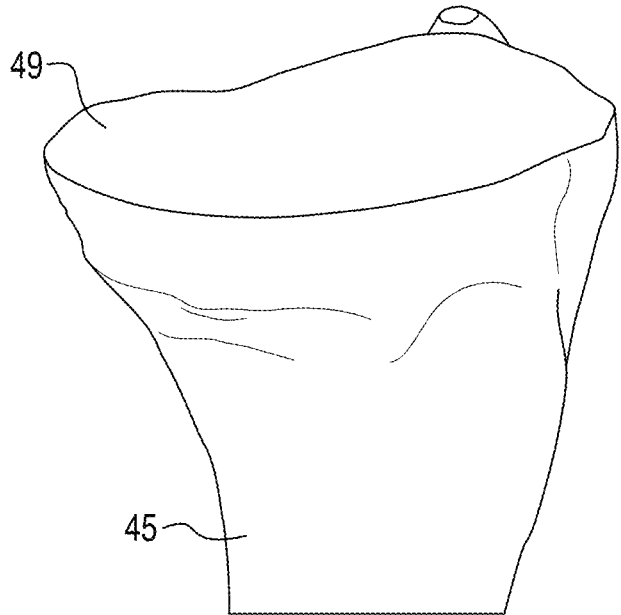

The surgeon can create a surgical plan based on the virtual bone model 45. The surgical plan may include the desired cuts, holes, or other modifications to a patient's bone 44 to be made by the surgeon using the surgical system 100. The modifications may be planned based on the configuration of a component to be coupled to the bone during the surgery. For example, prior to performance of total knee arthroplasty, the surgical plan may include the planned modifications to bone illustrated in FIGS. 3A-3D. FIGS. 3A and 3B illustrate a virtual bone model 45 of a femur 4 that includes planned modifications to the femur 4, including anterior cut 46, anterior chamfer cut 92, distal cut 84, posterior chamfer cut 94, and posterior cut 96. FIGS. 3C and 3D illustrate a virtual bone model 45 of a tibia 2 that includes planned modifications to the tibia 2, including tibial floor cut 49, a wall cut 51, and a peg cut 53. The planned modifications to the femur 4 shown in FIGS. 3A and 3B correspond to the virtual component 66 (FIG. 6A), which represents a component to be coupled to the femur 4.

Figure 13A:
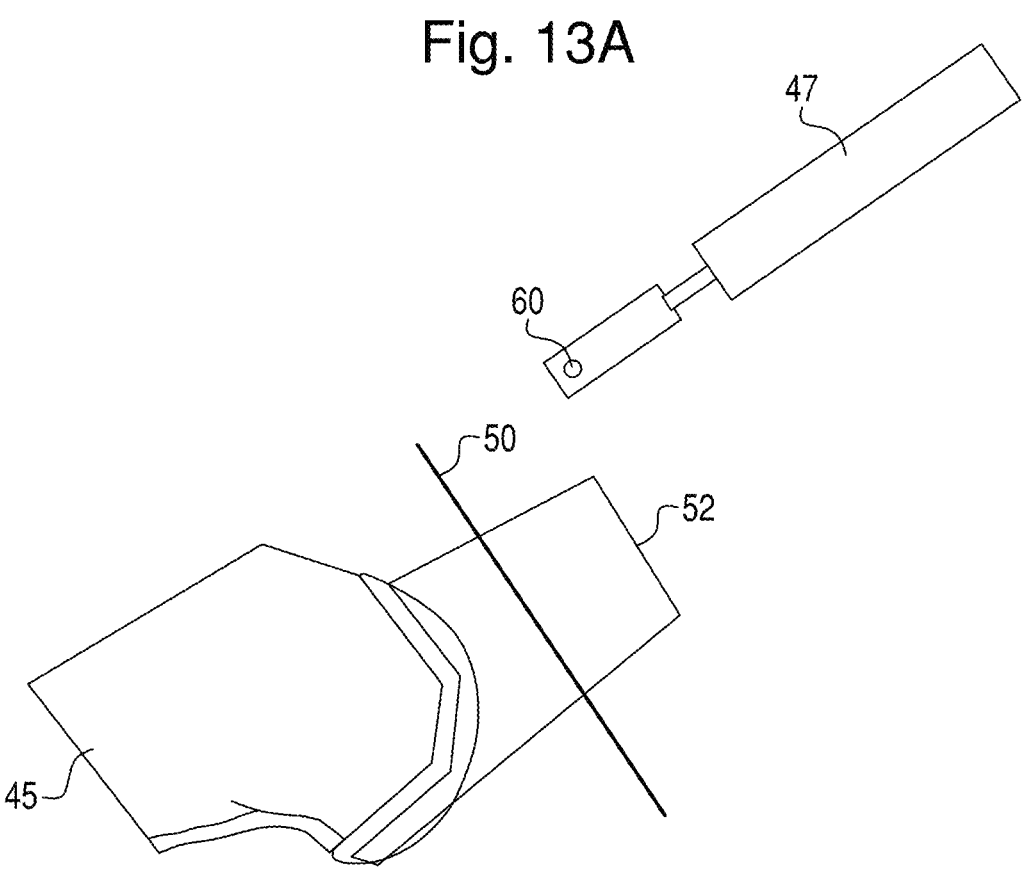
FIGS. 13A-13D illustrate entry and exit from haptic control when the haptic object is a three-dimensional volume, according to an exemplary embodiment.

The surgical plan further includes one or more haptic objects that will assist the surgeon during implementation of the surgical plan by enabling constraint of the surgical tool 36 during the surgical procedure. A haptic object 52 may be formed in one, two, or three dimensions. For example, a haptic object can be a line (FIG. 11A), a plane (FIG. 6B), or a three-dimensional volume (FIG. 13A). Haptic object 52 may be curved or have curved surfaces, and can be any shape. Haptic object 52 can be created to represent a variety of desired outcomes for movement of the surgical tool 36 during the surgical procedure. For example, a haptic object 52 in the form of a line may represent a trajectory of the surgical tool 36. A planar haptic object 52 may represent a modification, such as a cut, to be created on the surface of a bone 44. One or more of the boundaries of a three-dimensional haptic object may represent one or more modifications, such as cuts, to be created on the surface of a bone 44. Furthermore, portions of a three-dimensional haptic object may correspond to portions of bone to be removed during the surgical procedure.

Prior to performance of the surgical procedure, the patient's anatomy is registered to the virtual bone model 45 of the patient's anatomy by any known registration technique. One possible registration technique is point-based registration, as described in U.S. Pat. No. 8,010,180, titled "Haptic Guidance System and Method," granted Aug. 30, 2011, and hereby incorporated by reference herein in its entirety. Alternatively, registration may be accomplished by 2D/3D registration utilizing a hand-held radiographic imaging device, as described in U.S. application Ser. No. 13/562,163, titled "Radiographic Imaging Device," filed Jul. 30, 2012, and hereby incorporated by reference herein in its entirety. Registration of the patient's anatomy allows for accurate navigation and haptic control during the surgical procedure. When the patient's anatomy moves during the surgical procedure, the surgical system 100 moves the virtual bone model 45 in correspondence. The virtual bone model 45 therefore corresponds to, or is associated with, the patient's actual (i.e. physical) anatomy. Similarly, any haptic objects 52 created during surgical planning also move in correspondence with the patient's anatomy, and the haptic objects 52 correspond to locations in actual (i.e. physical) space. These locations in physical space are referred to as working boundaries. For example, a linear haptic object 52 corresponds to a linear working boundary in physical space, a planar haptic object 52 corresponds to a planar working boundary in physical space, and a three-dimensional haptic object 52 corresponds to a three-dimensional volume in physical space.

Figure 11A:
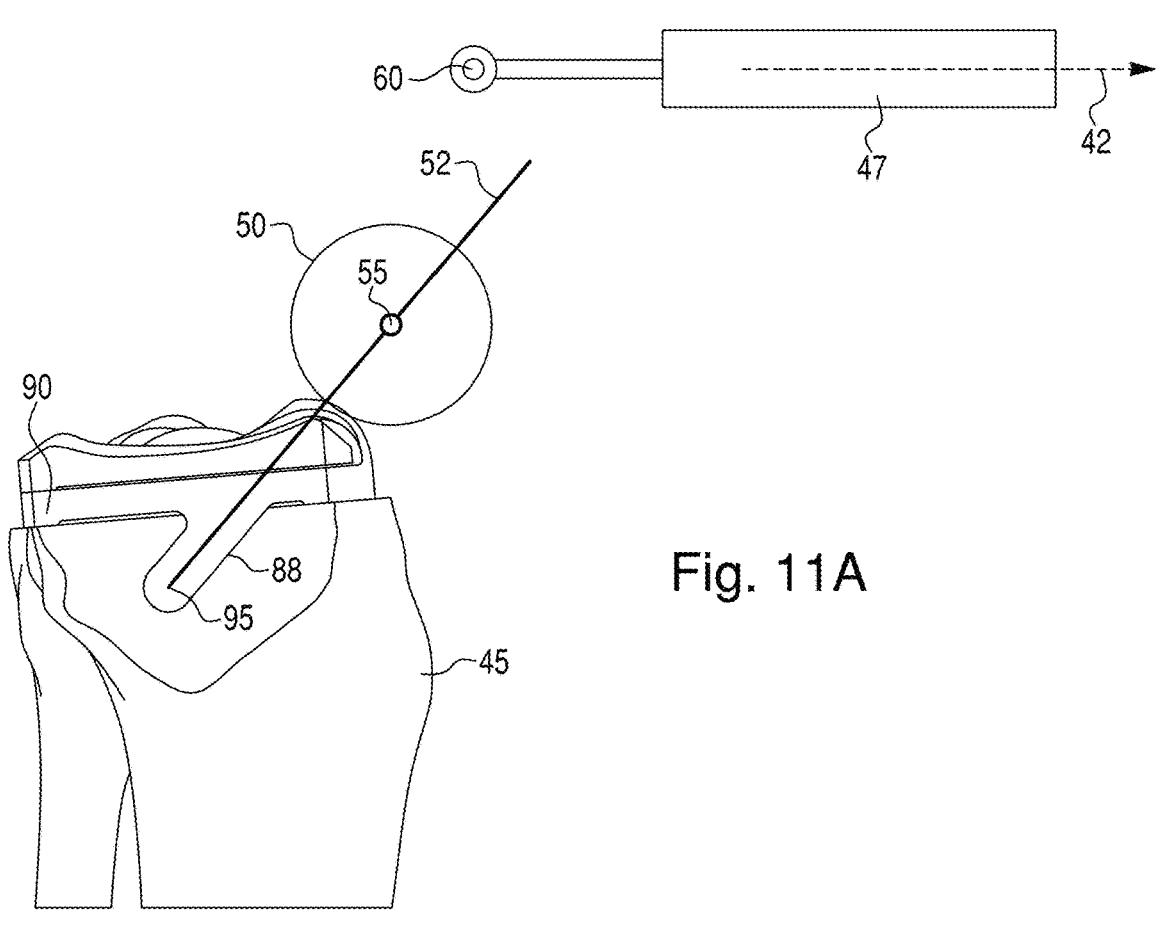
FIGS. 11A-11E illustrate entry and exit from haptic control when the haptic object is a line, according to an exemplary embodiment.

The surgical system 100 further includes a virtual tool 47 (FIG. 5A), which is a virtual representation of the surgical tool 36. Tracking of the surgical tool 36 by the navigation system 10 during a surgical procedure allows the virtual tool 47 to move in correspondence with the surgical tool 36. The virtual tool 47 includes one or more haptic interaction points (HIPs), which represent and are associated with locations on the physical surgical tool 36. As described further below, relationships between HIPs and haptic objects 52 enable the surgical system 100 to constrain the surgical tool 36. In an embodiment in which the surgical tool 36 is a spherical burr, an HIP 60 may represent the center of the spherical burr (FIG. 11A). If the surgical tool 36 is an irregular shape, such as sagittal saws 38 or 40 (FIGS. 2A and 2B), the virtual representation of the sagittal saw may include numerous HIPs. Using multiple HIPs to generate haptic forces (e.g. positive force feedback or resistance to movement) on a surgical tool is described in U.S. application Ser. No. 13/339,369, titled "System and Method for Providing Substantially Stable Haptics," filed Dec. 28, 2011, and hereby incorporated herein in its entirety. In one embodiment of the present invention, a virtual tool 47 representing a sagittal saw includes eleven HIPs. As used herein, references to an "HIP" are deemed to also include references to "one or more HIPs." For example, HIP 60 can represent one or more HIPs, and any calculations or processes based on HIP 60 include calculations or processes based on multiple HIPs.

During a surgical procedure, the surgical system 100 constrains the surgical tool 36 based on relationships between HIPs and haptic objects 52. In general, the term "constrain," as used herein, is used to describe a tendency to restrict movement. However, the form of constraint imposed on surgical tool 36 depends on the form of the relevant haptic object 52. A haptic object 52 may be formed in any desirable shape or configuration. As noted above, three exemplary embodiments include a line, plane, or three-dimensional volume. In one embodiment, the surgical tool 36 is constrained because HIP 60 of surgical tool 36 is restricted to movement along a linear haptic object 52. In another embodiment, the surgical tool 36 is constrained because planar haptic object 52 substantially prevents movement of HIP 60 outside of the plane and outside of the boundaries of planar haptic object 52. The boundaries of the planar haptic object 52 act as a "fence" enclosing HIP 60. If the haptic object 52 is a three-dimensional volume, the surgical tool 36 may be constrained by substantially preventing movement of HIP 60 outside of the volume enclosed by the walls of the three-dimensional haptic object 52. Because of the relationship between the virtual environment (including the virtual bone model 45 and the virtual tool 47) and the physical environment (including the patient's anatomy and the actual surgical tool 36), constraints imposed on HIP 60 result in corresponding constraints on surgical tool 36.

Haptic Control During a Surgical Procedure

At the start of a surgical procedure, the haptic device 30 (coupled to a surgical tool 36) is typically in free mode. The surgeon is therefore able to move the surgical tool 36 towards bone 44 in preparation for creation of a planned modification, such as a cut or hole. Various embodiments presented herein may facilitate the switch of haptic device 30 from free mode to haptic control mode and from haptic control mode back to free mode, which may increase the efficiency and ease of use of surgical system 100.

Figure 4:
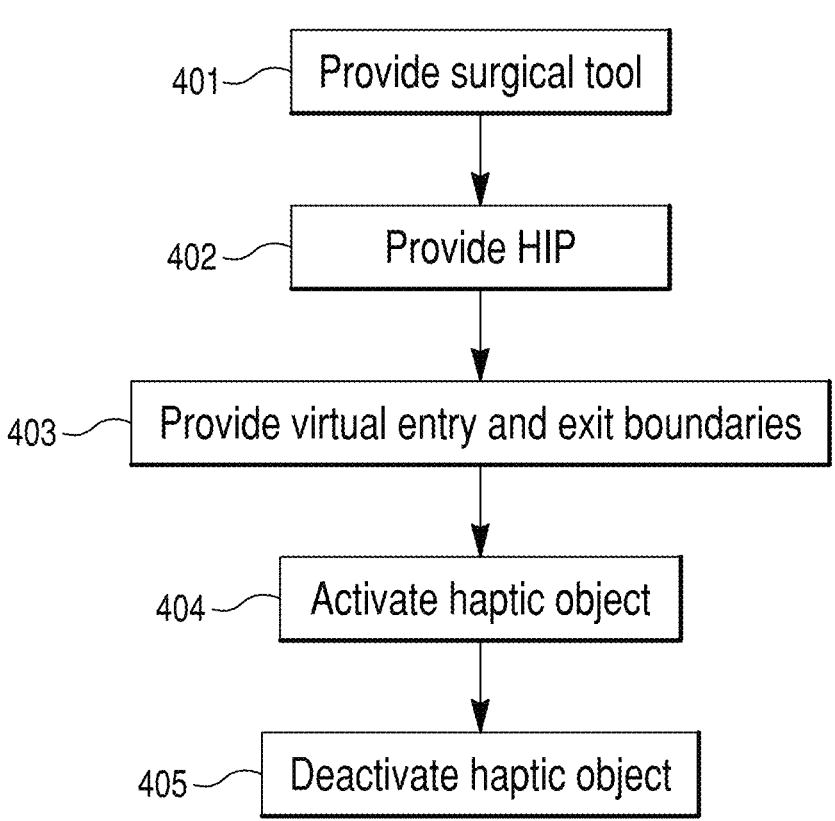
FIG. 4 illustrates a method for using a surgical system, according to an exemplary embodiment.

One method for using a surgical system is illustrated in FIG. 4. In step 401, a surgical tool is provided. A virtual HIP is also provided, which is associated with the surgical tool (e.g., surgical tool 36 of FIG. 1) such that movement of the HIP corresponds to movement of the surgical tool 36 (step 402). The surgical method further includes providing a virtual entry boundary and a virtual exit boundary (step 403). As described further below, entry and exit boundaries are virtual boundaries created during surgical planning, and interactions between an HIP and the entry and exit boundaries may facilitate switching haptic device 30 between free mode and haptic control mode during a surgical procedure. In other words, interactions between the HIP and entry and exit boundaries facilitate entry into and exit from haptic control. In step 404, a haptic object is activated. The activated haptic object can constrain the surgical tool after the haptic interaction point crosses the virtual entry boundary. In step 405, the haptic object is deactivated after the HIP crosses the virtual exit boundary. Because the haptic object may be deactivated substantially simultaneously with the HIP crossing the virtual exit boundary, the term "after" can include deactivation that occurs at substantially the same time as the HIP crosses the virtual exit boundary.

Figure 2A:
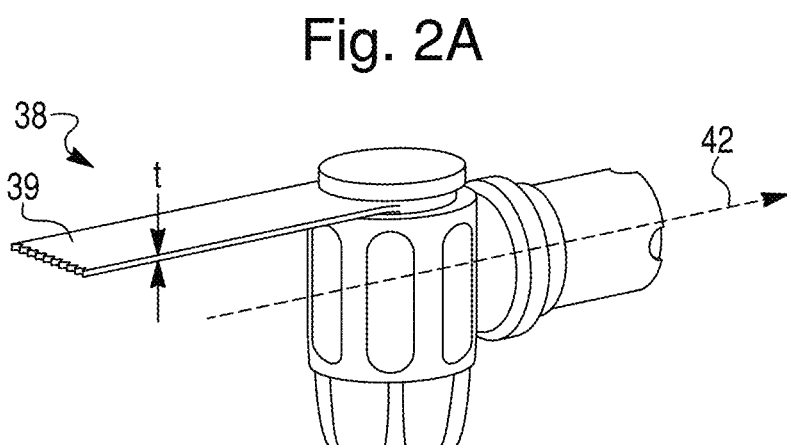
FIGS. 2A and 2B are embodiments of a sagittal saw.

FIGS. 5A-5E illustrate the virtual environment during an embodiment of entry into and exit from haptic control. In this embodiment, the virtual bone model 45 represents a femur 4, and virtual tool 47 represents a surgical tool 36 in the form of sagittal saw 38 (e.g. as shown in FIG. 2A). A sagittal saw 38 may be useful for creating a variety of cuts during a total knee arthroplasty, such as cuts corresponding to planned anterior cut 46, posterior cut 96, and tibial floor cut 49 (FIGS. 3A-3D). In the embodiment illustrated in FIGS. 5A-5E, the planned modification is anterior cut 46, which corresponds to the anterior surface 68 of a virtual implant component 66 (FIG. 6A). FIG. 3B shows a perspective view of the planned anterior cut 46 on a virtual bone model 45. The virtual environment depicted in FIG. 5A includes a planar haptic object 52. Planar haptic object 52 may also be an offset haptic object 78 (described below). Planar haptic object 52 may be any desired shape, such as the shape shown in FIG. 6B. FIG. 6B illustrates haptic object 52, a blade of virtual tool 47, and a virtual implant component 66 all superimposed on each other to aid in understanding the relationship between the various components of the surgical plan. In this embodiment, haptic object 52 represents a cut to be created on femur 4. Haptic object 52 is therefore shown in FIGS. 6A and 6B aligned with anterior surface 68 of the virtual implant component 66. The blade of virtual tool 47 is shown during haptic control mode, when haptic object 52 is activated and the blade is confined to the plane of haptic object 52.

Referring again to FIG. 5A, entry boundary 50 is a virtual boundary created during development of the surgical plan. Interactions between HIP 60 and the entry boundary 50 trigger the haptic device 30 to switch from free mode to "automatic alignment mode," a stage of haptic control described more fully below. The entry boundary 50 represents a working boundary in the vicinity of the patient's anatomy, and is designed and positioned such that the surgeon is able to accurately guide the surgical tool 36 to the working boundary when the haptic device 30 is in free mode. The entry boundary 50 may, but does not necessarily, enclose a portion of a haptic object 52. For example, in FIG. 5A, entry boundary 50 encloses a portion of haptic object 52.

Figure 5A:
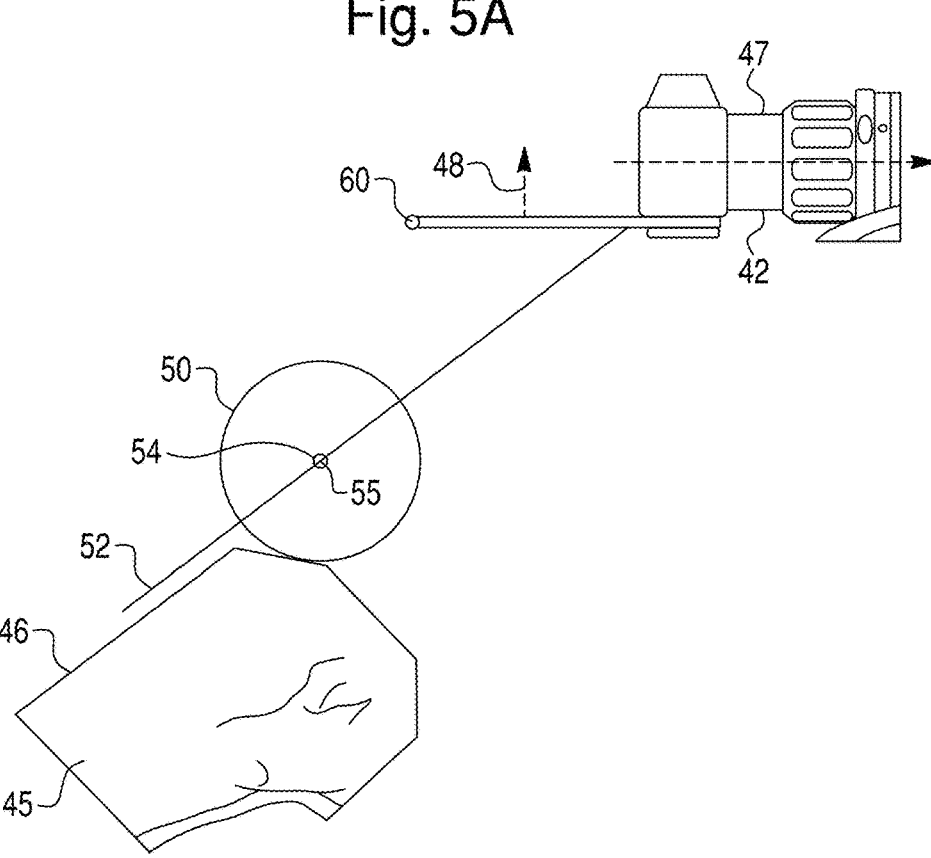
FIGS. 5A-5E illustrate entry and exit from haptic control when the tool normal is perpendicular to the haptic object, according to an exemplary embodiment.
Figure 6A:
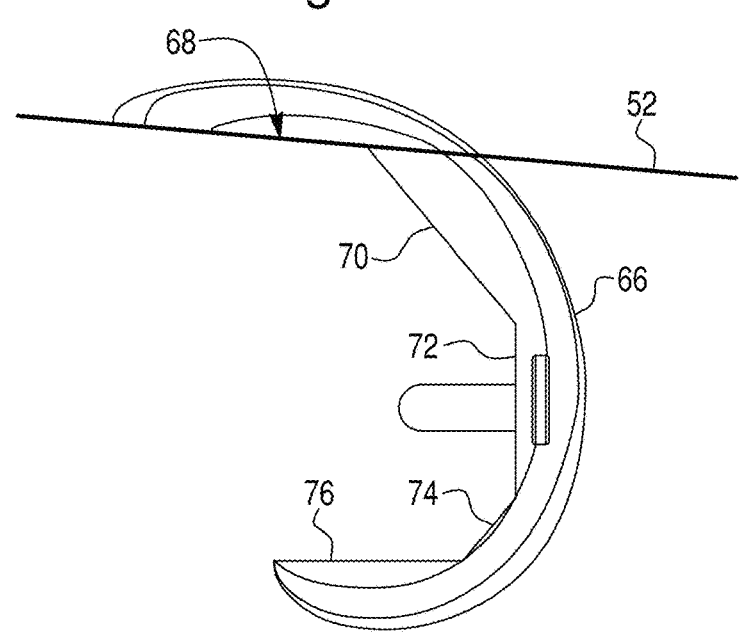
FIGS. 6A and 6B show the haptic object of FIGS. 5A-5E, according to an exemplary embodiment.
Figure 6B:
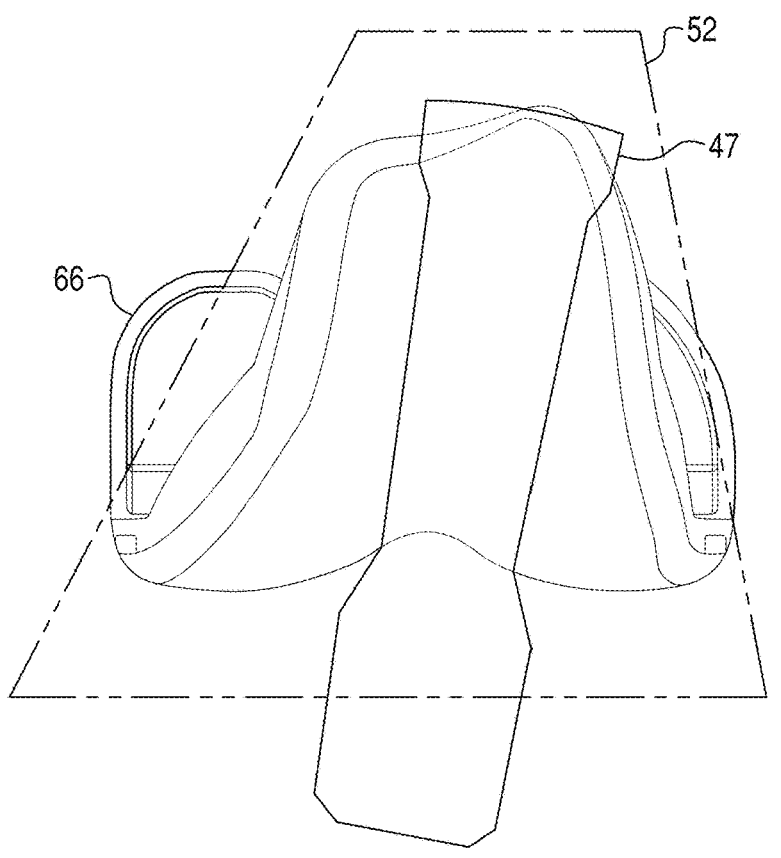

FIG. 5A presents a cross-section of the virtual environment. In this embodiment, entry boundary 50 is pill-shaped and encloses a three-dimensional volume. The pill-shaped entry boundary 50 has a cylindrical portion with a radius R (shown in FIG. 7A) and two hemispherical ends also having radius R (not shown). A target line 54 forms the cylinder axis (perpendicular to the page in FIG. 5A). The target line 54 passes through a target point 55, which is the center of entry boundary 50 in the illustrated cross section. Entry boundary 50 can also be any other shape or configuration, such as a sphere, a cube, a plane, or a curved surface.

Figure 16:
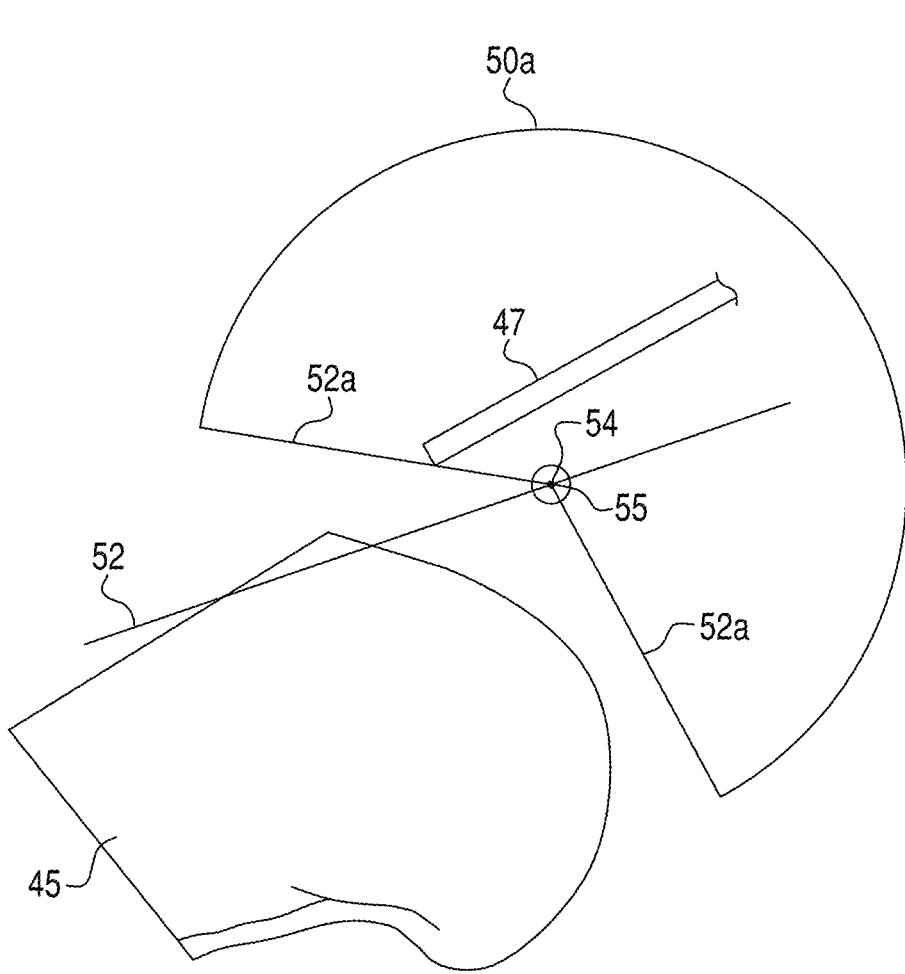
FIG. 16 illustrates an entry boundary, according to an exemplary embodiment.

In one embodiment, entry boundary 50 can be a "Pacman-shaped" entry boundary 50a, as shown in FIG. 16. The Pacman-shaped entry boundary is formed by cutting out a segment of a pill-shaped entry boundary, as described above, to form an entry boundary 50a having the cross section shown in FIG. 16. In this embodiment, the entry boundary 50a is therefore a three-dimensional volume shaped as a pill with a removed segment, such that a cross section of the virtual entry boundary is sector-shaped (i.e., "Pacman-shaped"). Pacman-shaped entry boundary 50a includes two intersecting haptic walls 52a. A target line 54 (perpendicular to the page in FIG. 16) represents the intersection of haptic walls 52a. Target point 55 is the center of target line 54. Haptic walls 52a are an embodiment of the haptic objects 52 described herein, and can therefore constrain movement of a surgical tool 36 by substantially preventing HIP 60 from crossing haptic walls 52a. Haptic walls 52 allow the Pacman-shaped entry boundary 50a to create a safe zone in front of the patient's bone. The Pacman-shaped entry boundary 50a can be used as the entry boundary in any of the embodiments described herein to protect the patient's bone when a surgical tool is approaching the patient. FIG. 16 illustrates virtual tool 47 (which corresponds to surgical tool 36) as it makes contact with haptic wall 52a. The haptic wall 52a prevents the virtual tool 47 (and thus the surgical tool 36) from crossing haptic wall 52a and approaching the patient's bone.

Figure 11B:
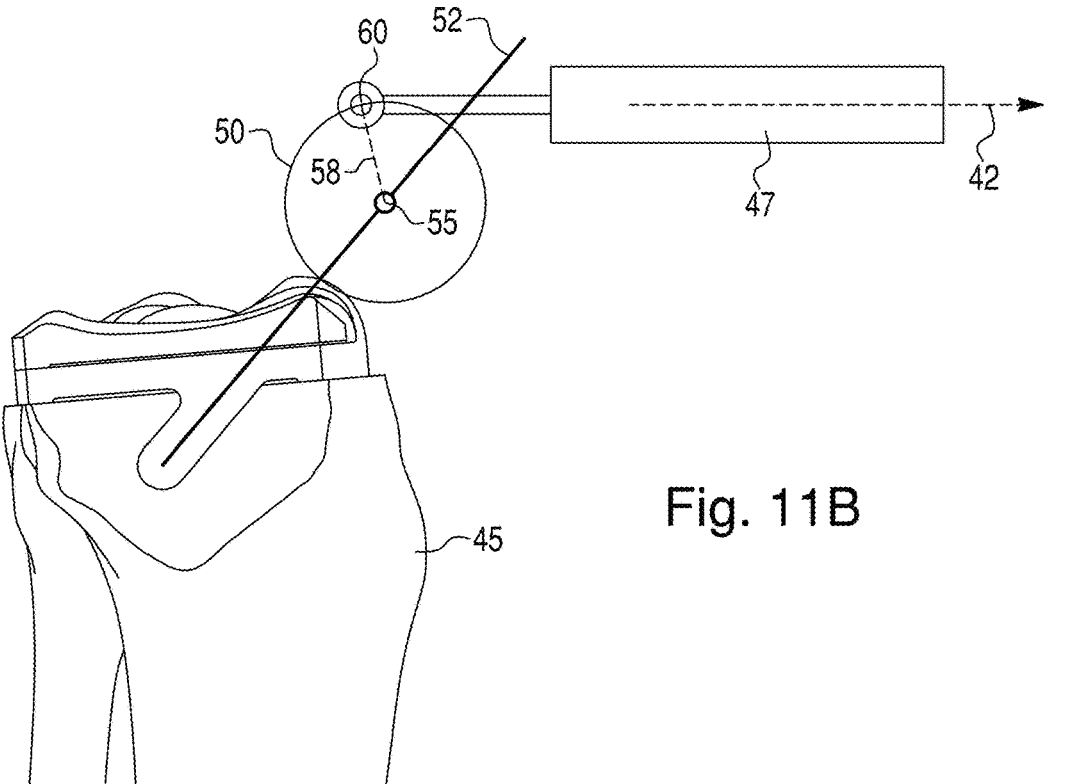

At the beginning of a surgical procedure, the surgeon guides surgical tool 36 towards the working boundary represented by entry boundary 50. Once the surgeon causes HIP 60 of the surgical tool 36 to cross entry boundary 50, the surgical system 100 enters automatic alignment. Prior to or during automatic alignment, the surgical system 100 performs calculations to reposition and reorient surgical tool 36. In one embodiment, the calculations include computing distance 58 (see FIG. 5B). If the surgical tool 36 is a spherical burr, distance 58 may represent the shortest distance line between a single HIP 60 and target line 54 (e.g. as shown in FIG. 11B) or another reference object. When the surgical tool 36 is a sagittal saw 38 or 40, the calculations to reposition and reorient surgical tool 36 may be based on the position of multiple HIPs relative to target line 54 or other reference object, although a distance 58 may still be calculated.

Figure 5B:
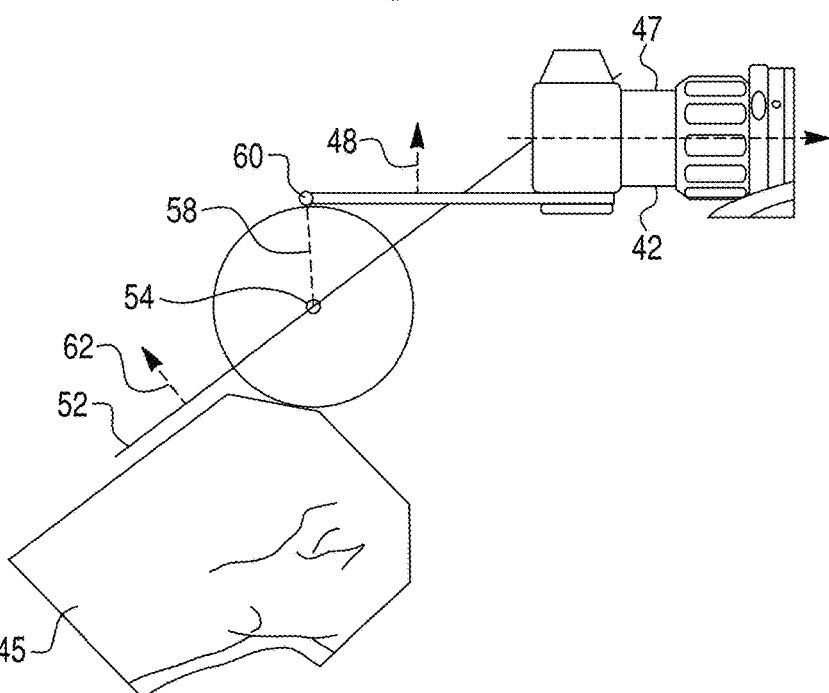
Figure 5C:
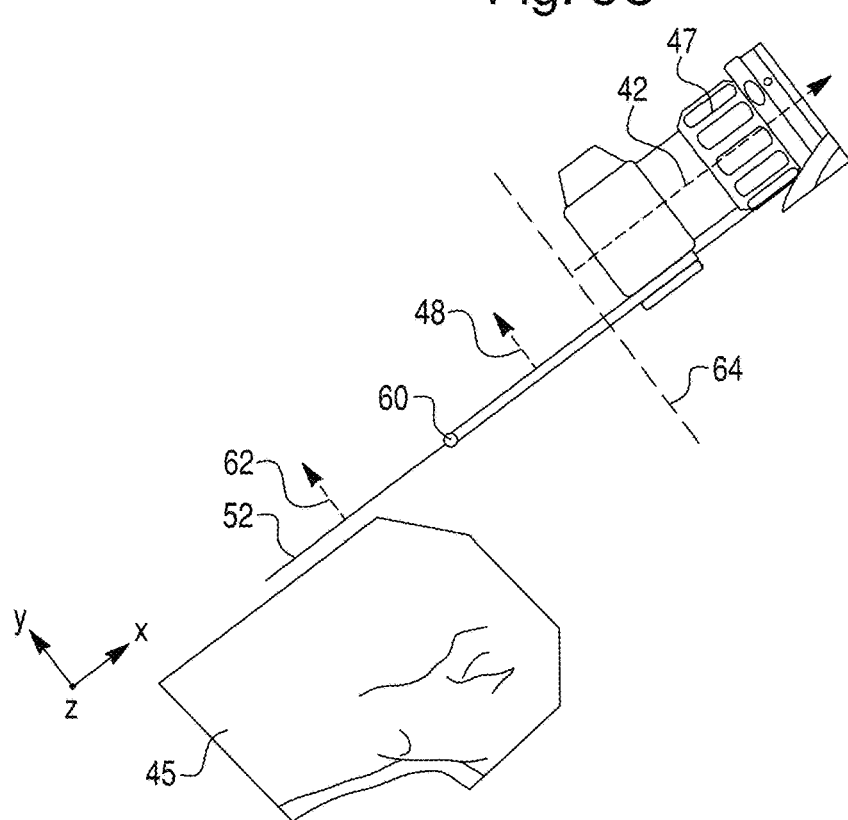

After performing the necessary calculations, the surgical system 100 is able to automatically align the surgical tool 36 from the pose of virtual tool 47 shown in FIG. 5B to the pose of virtual tool 47 shown in FIG. 5C. The haptic control embodiments described herein may (1) automatically modify the position of surgical tool 36 (i.e. reposition), (2) automatically modify the orientation of surgical tool 36 (i.e. reorient), or (3) both automatically reposition and reorient the surgical tool 36. The phrase "automatic alignment" can refer to any of scenarios (1), (2), or (3), and is a general term for modifying either or both of the position and orientation of the surgical tool 36. In the embodiment of FIGS. 5A-5E, for example, automatic alignment may alter both the position and the orientation of surgical tool 36 relative to a bone 44. Repositioning is accomplished by moving HIP 60 such that HIP 60 lies within the plane of haptic object 52. In one embodiment, HIP 60 is repositioned to lie on target line 54. Reorienting the surgical tool 36 may be accomplished by rotating the virtual tool 47 such that the virtual tool normal 48 is perpendicular to haptic object 52 (i.e. tool normal 48 is parallel to the haptic object normal 62), as shown in FIG. 5C. When the virtual tool 47 represents sagittal saw 38, aligning the virtual tool normal 48 perpendicular to haptic object 52 causes the blade 39 of sagittal saw 38 to be accurately oriented relative to the bone 44. However, if the cutting portion of surgical tool 36 is symmetrical, such as when surgical tool 36 is a spherical burr, it may not be necessary to reorient the surgical tool 36 during automatic alignment. Rather, surgical tool 36 might only be repositioned to bring HIP 60 within the plane of haptic object 52. After automatic alignment is complete, surgical tool 36 is in place to perform a bone modification according to the preoperative surgical plan.

The surgical system 100 may include a safety mechanism to provide the surgeon with control during automatic alignment. The safety mechanism can be designed to require certain actions (or continuation of an action) by a user for completion of automatic alignment. In one embodiment, the surgical system 100 produces an audible noise or other alert when HIP 60 crosses entry boundary 50. The surgical system 100 is then able to initiate automatic alignment. However, before an automatic alignment occurs, the surgeon must act by depressing a trigger or performing another action. If the trigger is released during automatic alignment, the surgical system 100 may stop any automatic movement of haptic device 30 or cause haptic device 30 to enter free mode. In another embodiment, haptic device 30 includes a sensor to sense when the surgeon's hand is present. If the surgeon removes his or her hand from the sensor during automatic alignment, the surgical system 100 may stop any automatic movement of haptic device 30 or cause haptic device 30 to enter free mode. The surgeon acts to ensure completion of automatic alignment by continuing to keep his or her hand on the sensor. These embodiments of a safety mechanism allow the surgeon to decide whether and when to enable automatic alignment, and further allows the surgeon to stop automatic alignment if another object (e.g. tissue, an instrument) is in the way of surgical tool 36 during automatic alignment.

Entry boundary 50a of FIG. 16 is particularly beneficial if the above-described safety mechanisms are being utilized. As one illustration, the surgeon begins the haptic control processes described herein by guiding surgical tool 36 towards the patient until the surgical tool 36 penetrates an entry boundary. The surgical system 100 then alerts the surgeon that the system is ready to begin automatic alignment. However, the surgeon may not immediately depress a trigger or perform some other action to enable the system to initiate the automatic alignment mode. During this delay, the surgical tool 36 remains in free mode, and the surgeon may continue to guide the tool towards the patient. Accordingly, entry boundary 50a shown in FIG. 16 includes haptic walls 52a. These walls 52a prevent the surgeon from continuing to guide the surgical tool 36 (represented by virtual tool 47) towards the patient prior to enabling automatic alignment (e.g., via depressing a trigger or placing a hand on a sensor). The haptic walls 52a therefore serve as a safety mechanism to protect the patient prior to the surgical tool 36 being appropriately positioned and oriented to perform the planned bone modifications.

Referring to FIG. 5C, automatic alignment is complete and the pose of surgical tool 36 has been correctly modified, and the haptic device 30 remains in haptic control mode. Haptic control mode, in general, can be characterized by the activation of a haptic object 52 and the imposition of a constraint on the movement of a surgical tool 36 by the haptic object 52. Automatic alignment can therefore be a form of haptic control because haptic object 52 is activated, and surgical tool 36 is constrained to specific movements to realign surgical tool 36 based on haptic object 52. During the stage of haptic control shown in FIG. 5C, haptic object 52 is activated and HIP 60 is constrained within the plane defined by haptic object 52. The surgeon can therefore move surgical tool 36 within the planar working boundary corresponding to haptic object 52, but is constrained (e.g., prevented) from moving the surgical tool 36 outside of the planar working boundary. The surgeon performs the planned cut during haptic control mode. As the surgeon is cutting, the virtual tool 47 can move in the x-direction from the position illustrated in FIG. 5C to the position illustrated in FIG. 5D. The virtual tool 47 may also move back and forth in the z-direction in correspondence with movement of surgical tool 36. However, planar haptic object 52 restricts HIP 60 (and thus surgical tool 36) from movement in the y-direction. FIG. 6B illustrates one embodiment of the shape of haptic object 52, shown with virtual tool 47 of FIG. 5C superimposed on haptic object 52. A surgeon can reposition sagittal saw 38 within the working boundary corresponding to haptic object 52, but the surgical system 100 prevents sagittal saw 38 from crossing the outer bounds of the working boundary. FIG. 6A is a view of haptic object 52 aligned with anterior surface 68 of a virtual implant component 66. As mentioned previously, the modifications to bone, and thus the haptic objects 52, are typically planned to correspond to the configuration of a component to be coupled to the bone during the surgical procedure.

Figure 5D:
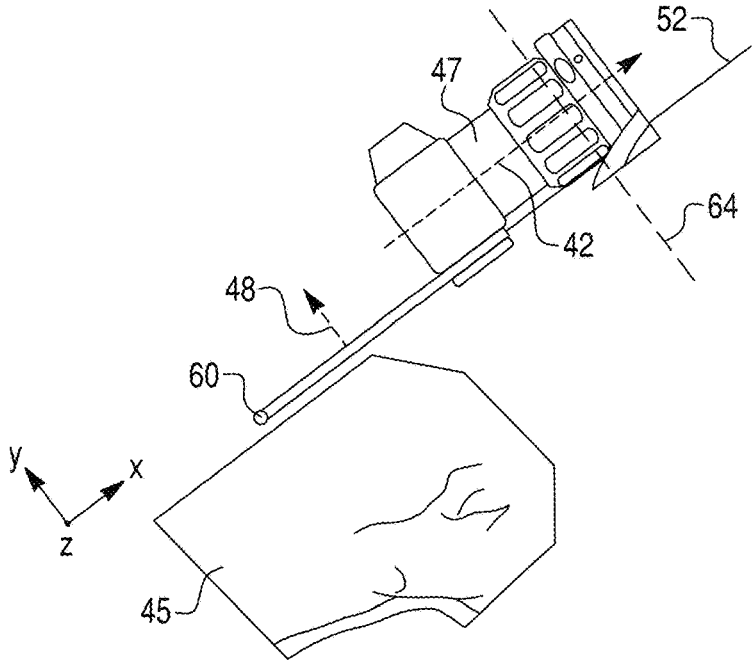
Figure 5E:
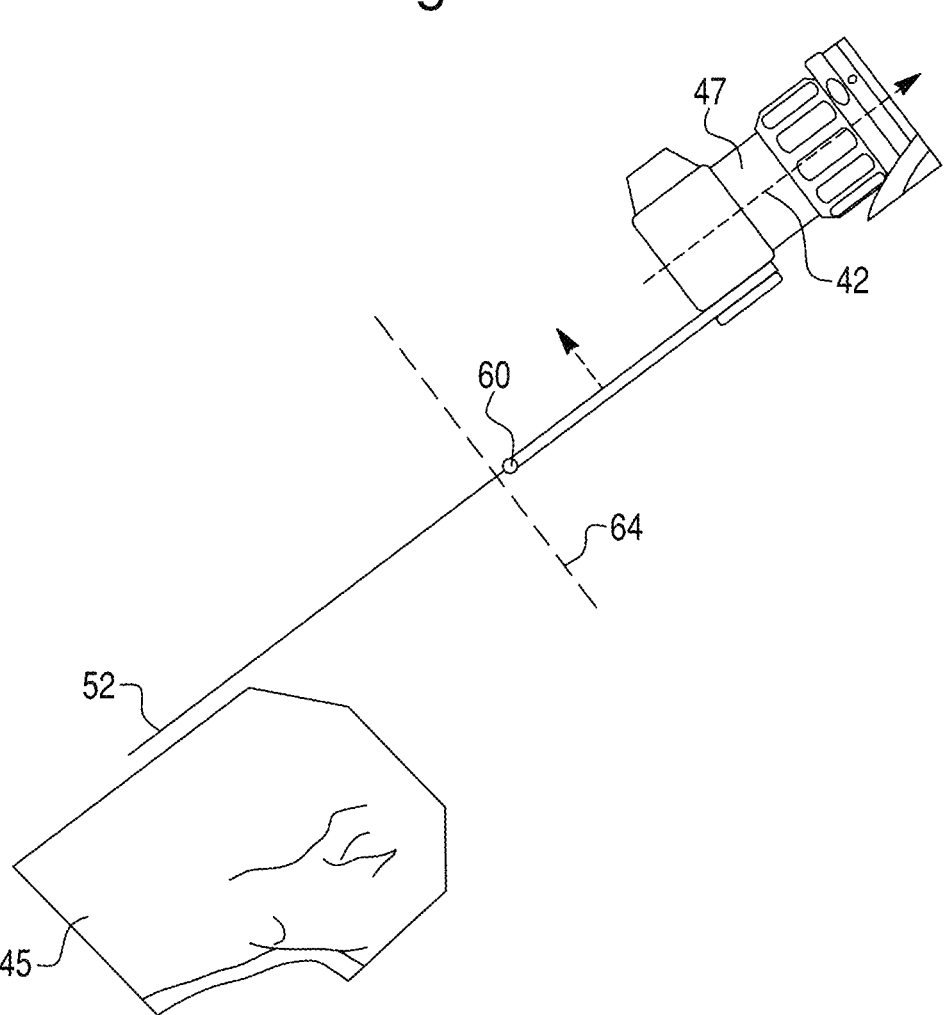

During portions of haptic control mode, an exit boundary 64 is activated (see FIGS. 5C-5E). The exit boundary 64, like the entry boundary 50, is a virtual boundary created during development of the surgical plan. Interactions between HIP 60 and exit boundary 64 deactivate haptic object 52 and trigger the haptic device 30 to switch from haptic control mode back to free mode. The surgical system therefore remains in haptic control mode and maintains surgical tool 36 within the working boundary corresponding to haptic object 52 until HIP 60 crosses the exit boundary 64. Once HIP 60 crosses the exit boundary 64 (e.g. by moving from the position shown in FIG. 5D to the position shown in FIG. 5E) the haptic object 52 deactivates and haptic device 30 switches from haptic control mode to free mode. When haptic control is released, the surgical tool 36 is no longer bound within the confines of a working boundary, but can be manipulated freely by the surgeon.

In one embodiment, the exit boundary 64 is planar, located a distance L from entry boundary 50 (see FIG. 7A), and has an exit normal 59. During haptic control mode, the surgical system 100 continuously calculates the distance from HIP 60 to exit boundary 64. Because exit normal 59 points away from the patient's anatomy, the distance from HIP 60 to the exit boundary 64 will typically be negative during performance of bone modifications (e.g. cutting, drilling). However, when the value of this distance becomes positive, haptic control is released by deactivation of haptic object 52, and the haptic device 30 enters free mode. In other embodiments, the exit boundary 64 can be curved, three-dimensional, or any configuration or shape appropriate for interacting with HIP 60 to disengage haptic control during a surgical procedure. Simultaneously or shortly after the switch to free mode, exit boundary 64 is deactivated and entry boundary 50 is reactivated. The surgeon can then reenter haptic control mode by causing surgical tool 36 to approach the patient such that HIP 60 crosses entry boundary 50. Thus, the surgeon can move back and forth between free mode and haptic control by manipulating surgical tool 36.

The entry boundary 50 and exit boundary 64 described in connection with the various embodiments herein provide advantages over prior art methods of haptic control. Some prior art embodiments employing haptic objects require a separate action by a user to activate and deactivate haptic objects and thus enter and exit haptic control. For example, to release an HIP from the confines of a haptic object, the user might have to press a button or perform a similar action to deactivate the haptic object. The action by the user deactivates the haptic object, which then allows the surgeon to freely manipulate the surgical tool. Use of an exit boundary as described herein eliminates the need for the surgeon to perform a separate deactivation step. Rather, the surgeon must only pull a surgical tool 36 away from the patient to automatically deactivate a haptic object 52 and exit haptic control. Embodiments of the present disclosure may therefore save time in the operating room. Furthermore, operation of a haptic device 30 may be more intuitive and user-friendly due to the surgeon being able to switch conveniently between free mode and haptic control mode.

Figure 7A:
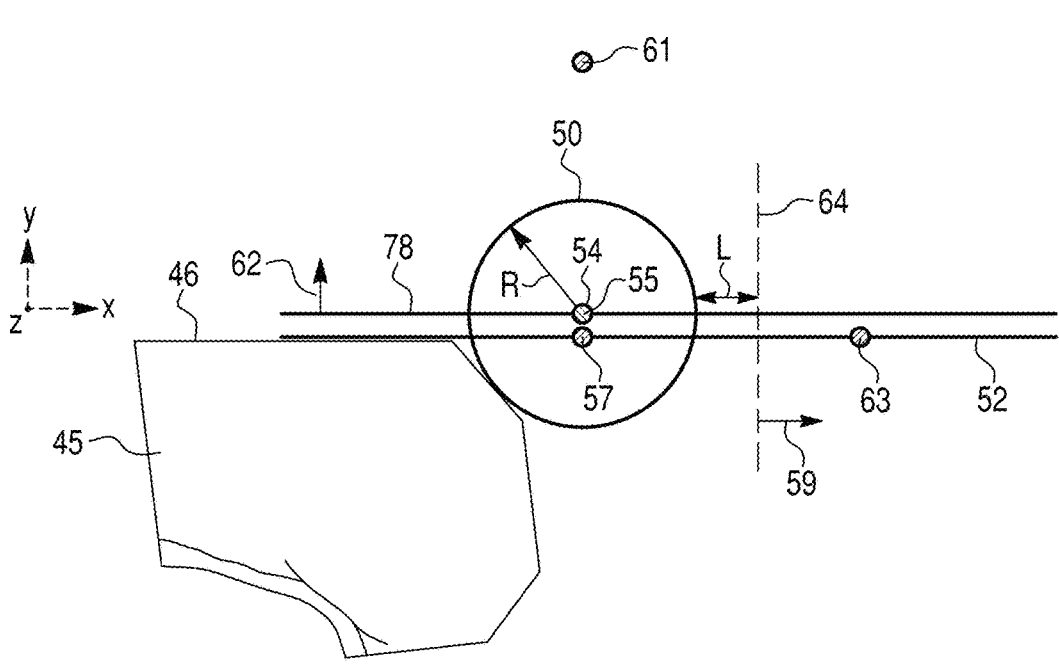
FIGS. 7A and 7B illustrate an offset haptic object according to an exemplary embodiment.
Figure 7B:
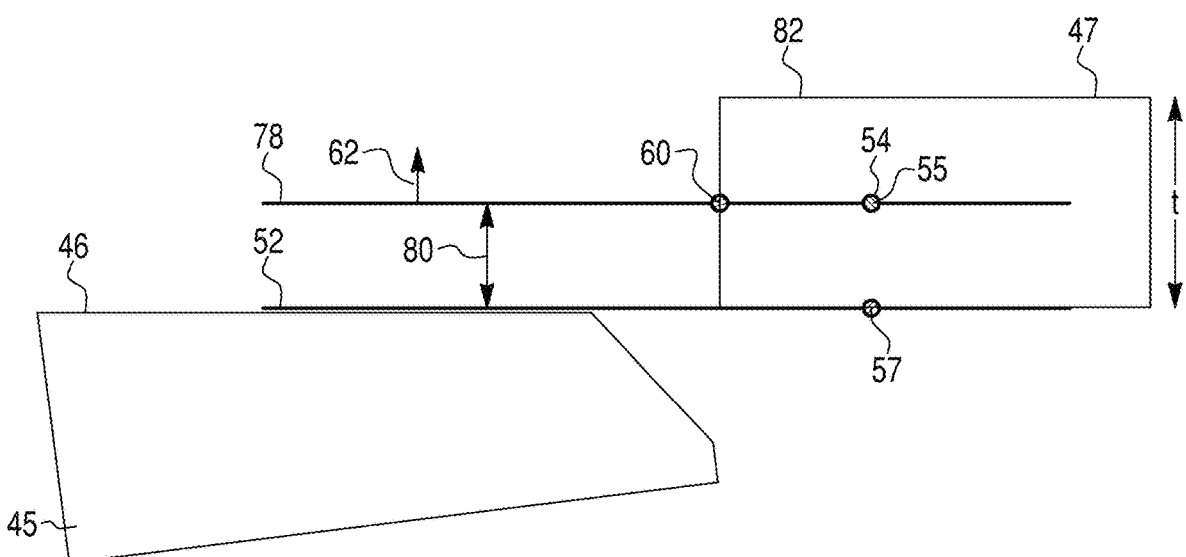

FIGS. 7A and 7B illustrate haptic object 52 and offset haptic object 78. A surgical plan may include an adjustable offset haptic object 78 to take into account characteristics of the surgical tool 36. Use of offset haptic object 78 during haptic control mode of the haptic device 30 may provide additional accuracy during the surgical procedure by accounting for the dimensions of the surgical tool 36. Thus, if the surgical tool 36 is a spherical burr, the offset haptic object 78 may be translated from haptic object 52 such that distance 80 (FIG. 7B) is equivalent to the radius of the spherical burr. When offset haptic object 78 is activated, the surgical system 100 constrains HIP 60 of the spherical burr within the bounds of planar offset haptic object 78, rather than constraining the HIP 60 of the spherical burr within the bounds of planar haptic object 52. When constrained by the offset haptic object 78, the edge of the spherical burr aligns with planned anterior cut 46. Similarly, if the surgical tool 36 is a sagittal saw 38, distance 80 may be equivalent to half the thickness t of blade 39. FIG. 7B illustrates virtual tool 47. In this embodiment, virtual tool 47 is the sagittal saw 38 of FIG. 2A and includes a virtual blade 82. The virtual blade 82 has a thickness t equivalent to the thickness of blade 39. When HIP 60 of virtual tool 47 is constrained to offset haptic object 78, the bottom edge of virtual blade 82 will align with planned anterior cut 46. The actual cut created by the sagittal saw 38 during surgery will then more closely correspond to the planned anterior cut 46 than if HIP 60 were constrained to haptic object 52 of FIG. 7B.

In various embodiments, the surgical system 100 utilizes factors related to implementation of the surgical plan when calculating the parameters of adjustable offset haptic object 78. One factor may be the vibrations of the surgical tool 36 during surgery, which can cause a discrepancy between the actual dimensions of a surgical tool 36 and the effective dimensions of the surgical tool 36. For example, a spherical burr with a radius of 3 mm may remove bone as though its radius were 4 mm. The burr therefore has an effective radius of 4 mm. Similarly, due to vibrations, a blade 39 having a thickness of 2 mm may create a slot in bone having a thickness of 2.5 mm. The blade 39 therefore has an effective thickness of 2.5 mm. The offset haptic object 78 is created to take into account the effect of vibrations or other factors on surgical tool 36 to increase the accuracy of the actual bone modification created during surgery.

The offset haptic object 78 may be adjustable. Adjustability is advantageous because it allows a user to modify the offset haptic object 78 without having to redesign the original haptic object 52. The surgical system 100 may be programmed to allow easy adjustment by the user as new information is gathered prior to or during the surgical procedure. If the surgical plan includes offset haptic object 78, additional elements of the surgical plan may be similarly adjusted to an offset position from their originally planned positions. For example, the surgical system 100 may be programmed to translate entry boundary 50 and exit boundary 64 in the y-direction by the same distance as the offset haptic object 78 is translated from the haptic object 52. Similarly, target line 54 and target point 55 may also be offset from their initially planned position. It is to be understood that the "haptic object 52" referred to by many of the embodiments described herein may technically be an "offset haptic object" with respect to the original haptic object of the relevant surgical plan.

Figure 2B:
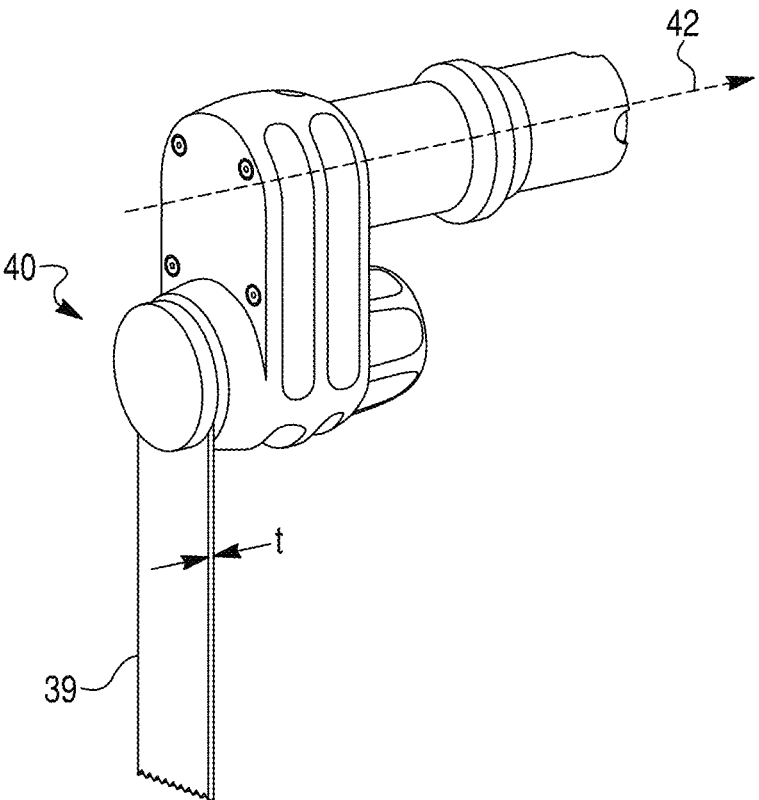
Figure 8C:
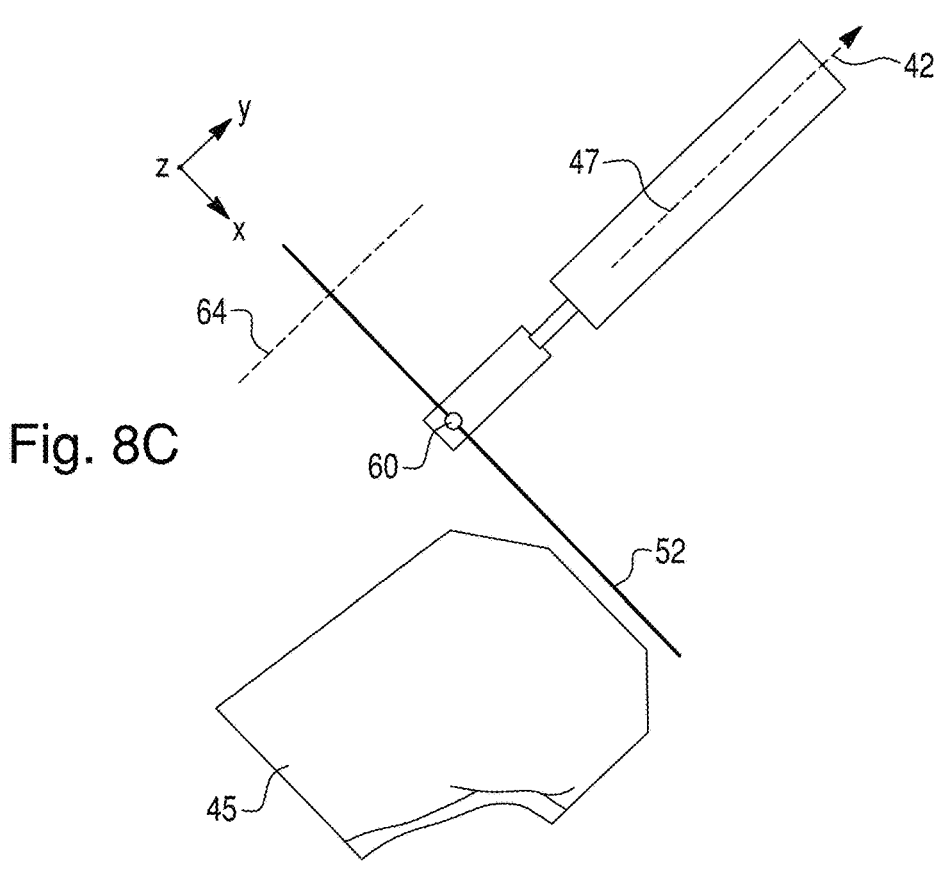
Figure 8D:
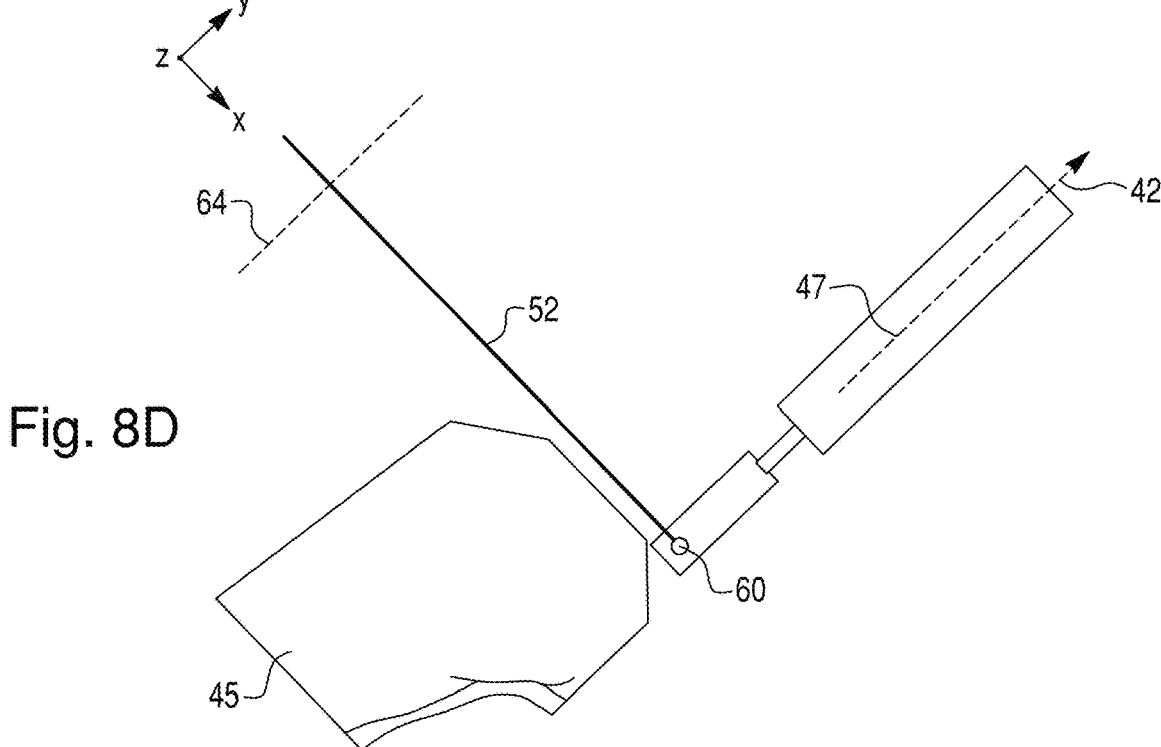
Figure 8E:
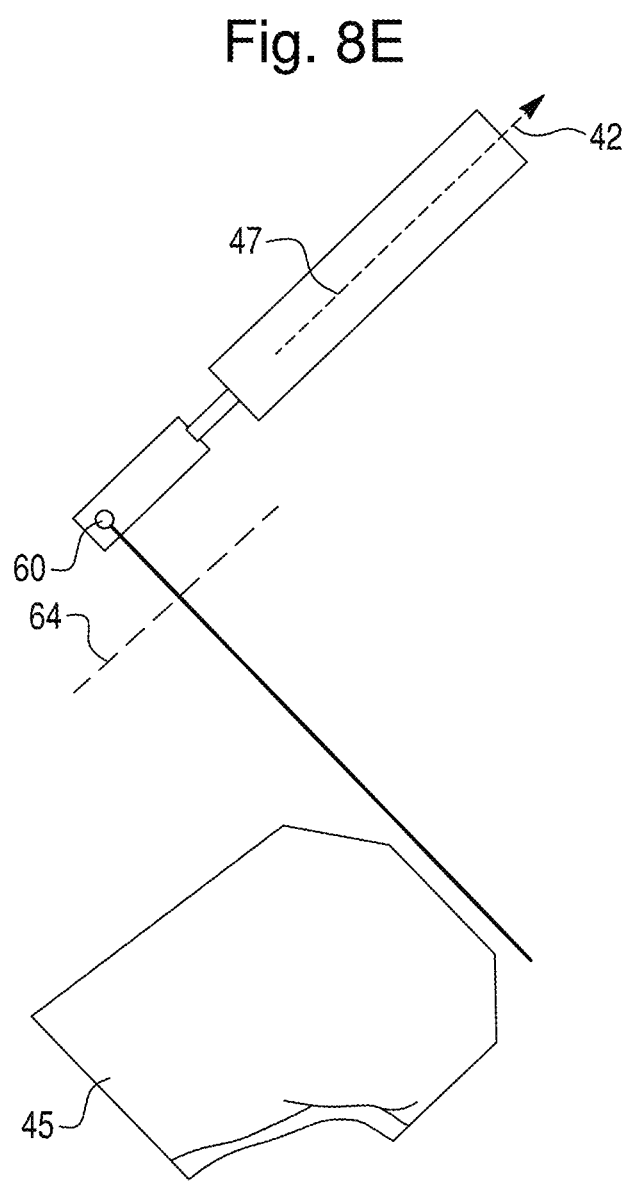
Figure 9A:
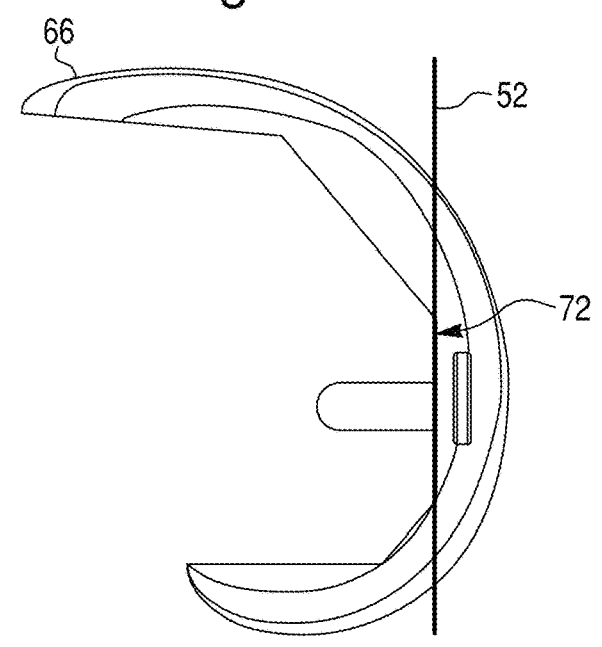
FIGS. 9A and 9B show the haptic object of FIGS. 8A-8E, according to an exemplary embodiment.
Figure 9B:
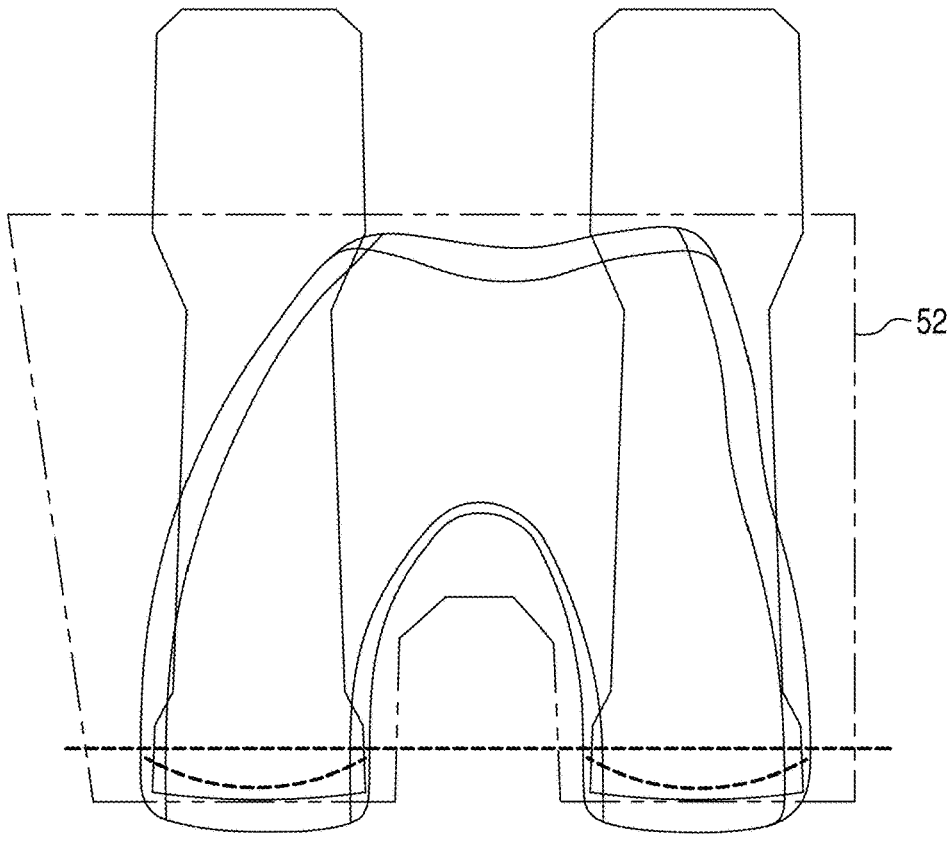

FIGS. 8A-8E illustrate the virtual environment during another embodiment of entry and exit from haptic control. In this embodiment, the virtual bone model 45 represents a femur 4. Virtual tool 47 represents a surgical tool 36 in the form of a sagittal saw 40 (e.g. as shown in FIG. 2B). A sagittal saw 40 may be useful for performing a variety of cuts during a total knee arthroplasty, such as cuts corresponding to planned distal cut 84 and anterior chamfer cut 92. In the embodiment of FIGS. 8A-8E, the planned modification is a planned distal cut 84, which corresponds to distal surface 72 of a virtual implant component 66 (FIG. 9A). A perspective view of planned distal cut 84 is shown in FIG. 3B. In this embodiment, as in the embodiment of FIGS. 5A-5E, haptic object 52 represents a cut to be created on femur 4. Haptic object 52 may be any shape developed during surgical planning, such as the shape shown in FIG. 9B.

Referring again to FIGS. 8A-8E, entry into and exit into haptic control takes place similarly as in the embodiment of FIGS. 5A-5E, differing primarily in the automatic alignment and resulting orientation of surgical tool 36. Any applicable features disclosed in connection to the embodiment of FIGS. 5A-5E may also be present in the embodiment of FIG. 8A-8E. In FIG. 8A, the haptic device 30 is in free mode and entry boundary 50 is activated. As the surgeon brings the surgical tool 36 towards the patient's anatomy, the virtual tool 47 correspondingly approaches entry boundary 50. Once HIP 60 has crossed entry boundary 50, the surgical system 100 enters automatic alignment, during which the surgical system 100 performs the necessary calculations and then modifies the position and orientation of surgical tool 36 (e.g. from FIG. 8B to FIG. 8C). The position is modified to bring HIP 60 to the target line 54, and the orientation is modified to bring tool axis 42 perpendicular to haptic object 52. Because the blade 39 of sagittal saw 40 (FIG. 2B) is perpendicular to the tool axis 42, aligning the tool axis 42 perpendicular to the haptic object 52 causes the blade to lie in the x-y plane during the surgical procedure. Orientation of the tool axis 42 in this embodiment contrasts to the embodiment of FIGS. 5A-5E, in which the tool axis 42 is oriented parallel to haptic object 52 during cutting (e.g., FIG. 5C).

The surgical plan may be developed such that the surgical system 100 will orient the surgical tool 36 in any desired direction relative to haptic object 52. The desired orientation may depend on the type of surgical tool. For example, if the surgical tool 36 is a sagittal saw, the surgical system 100 may orient the surgical tool 36 differently depending on the type of sagittal saw (e.g. sagittal saw 38 or sagittal saw 40) or the type of cut to be created. Furthermore, in some embodiments, the tool is repositioned but not reoriented during automatic alignment. For example, if the surgical tool 36 is a spherical burr, the surgical system 100 may not need to modify the orientation of the surgical tool 36 to obtain the desired bone modification.

Once the surgical tool 36 has been automatically aligned as shown in FIG. 8C, HIP 60 is constrained within the plane defined by haptic object 52. Entry into this stage of haptic control can trigger activation of exit boundary 64. The surgeon performs the cut by manipulating the surgical tool 36 within the planar working boundary corresponding to haptic object 52 in the x-direction and the z-direction. FIGS. 8C and 8D illustrate a change in position during cutting along the x-direction. When the surgeon moves the surgical tool 36 from the position shown in FIG. 8D to the position shown in FIG. 8E, HIP 60 crosses exit boundary 64. The interaction between HIP 60 and exit boundary 64 deactivates haptic object 52, releasing haptic control of surgical tool 36 and causing haptic device 30 to once again enter free mode. Upon crossing the exit boundary 64 or shortly thereafter, exit boundary 64 deactivates and entry boundary 50 reactivates. The surgeon can then reenter automatic alignment and haptic control during performance of bone modifications by manipulating surgical tool 36 such that HIP 60 crosses entry boundary 50.

Figure 10:
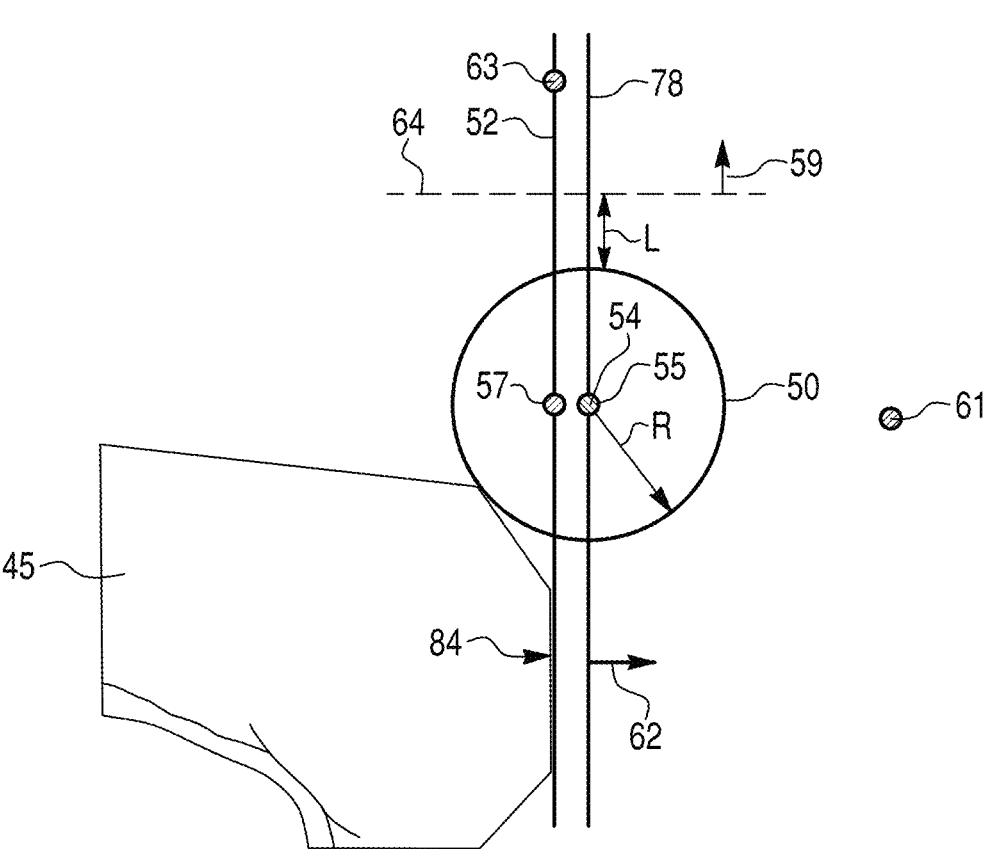
FIG. 10 illustrates another embodiment of an offset haptic object, according to an exemplary embodiment.

FIG. 10 illustrates haptic object 52 and offset haptic object 78 in relation to planned distal cut 84. As described in connection with FIGS. 7A and 7B, the adjustable offset haptic object 78 may be modified depending factors such as the dimensions of surgical tool 36 or other factors related to implementation of the surgical plan. The adjustment of offset haptic object 78 can lead to adjustment of other planned features of the virtual environment, such as entry boundary 50, target line 54, target point 55, and exit boundary 64.

The surgical plans depicted in FIGS. 7A-7B and 10 can be defined by various points and vectors. Normal origin point 57 lies on the original haptic object 52 and defines the origin of the haptic object normal 62 as well as the exit normal 59. The haptic normal point 61 further defines the haptic object normal 62, and may be located approximately 50 mm from the normal origin point 57. The exit normal point 63 further defines the exit normal 59, and may also be located approximately 50 mm from the normal origin point 57. Thus, the haptic object normal 62 can be defined as the vector direction from the normal origin point 57 to the haptic normal point 61, and the exit normal 59 can be defined as the vector direction from the normal origin point 57 to the exit normal point 63. The target point 55 may lie on the offset haptic object 78, and is offset from the normal origin point 57 in the direction of the haptic object normal 62 by a desired amount. As explained above, the desired amount may take into account the effective radius of a spherical burr or half of the effective thickness of a sagittal saw blade 39. The target line 54 can be defined by target point 55 and the cross product vector of exit normal 59 and haptic object normal 62, with endpoints on opposing edges of the offset haptic object 78.

Figure 11C:
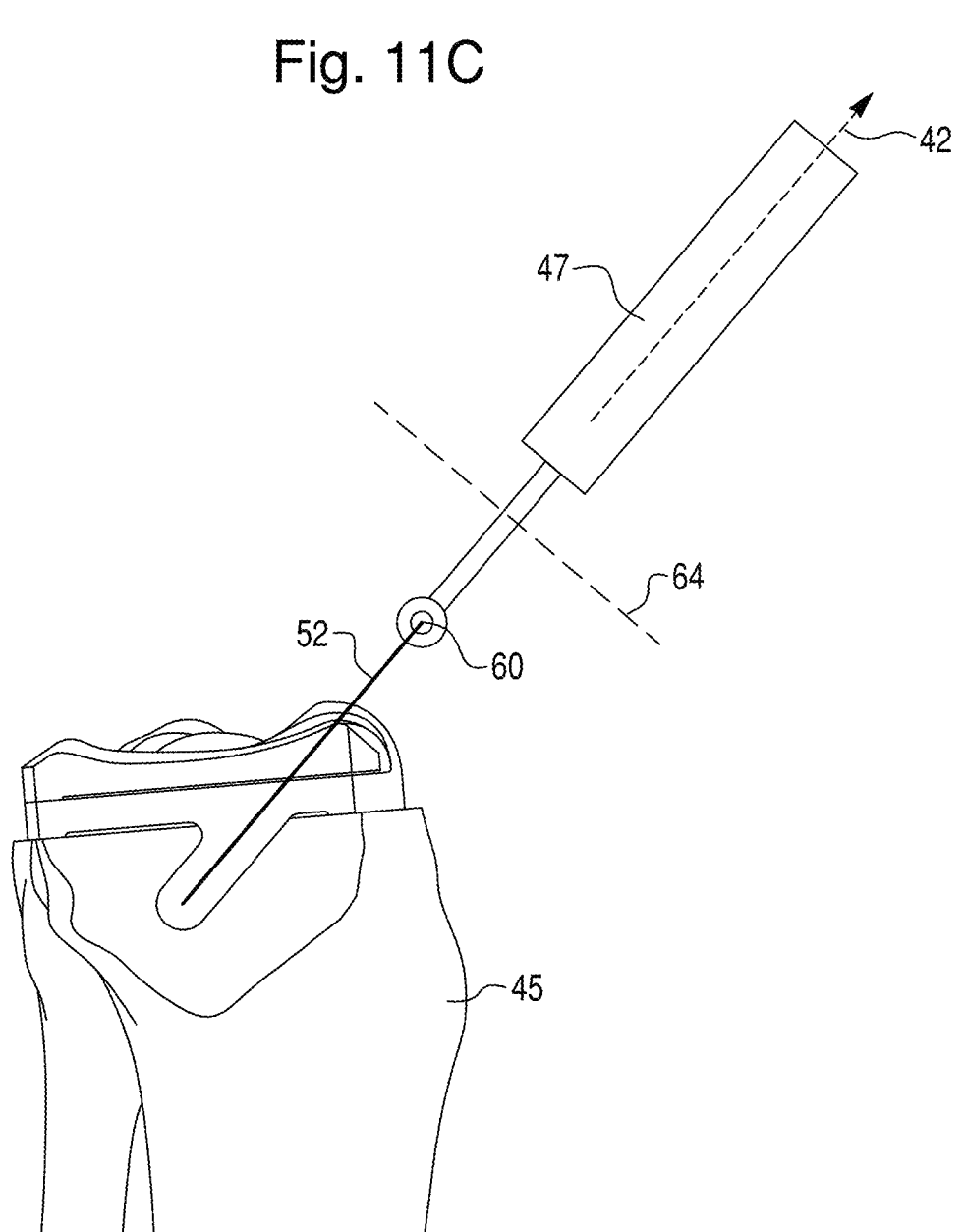
Figure 11D:
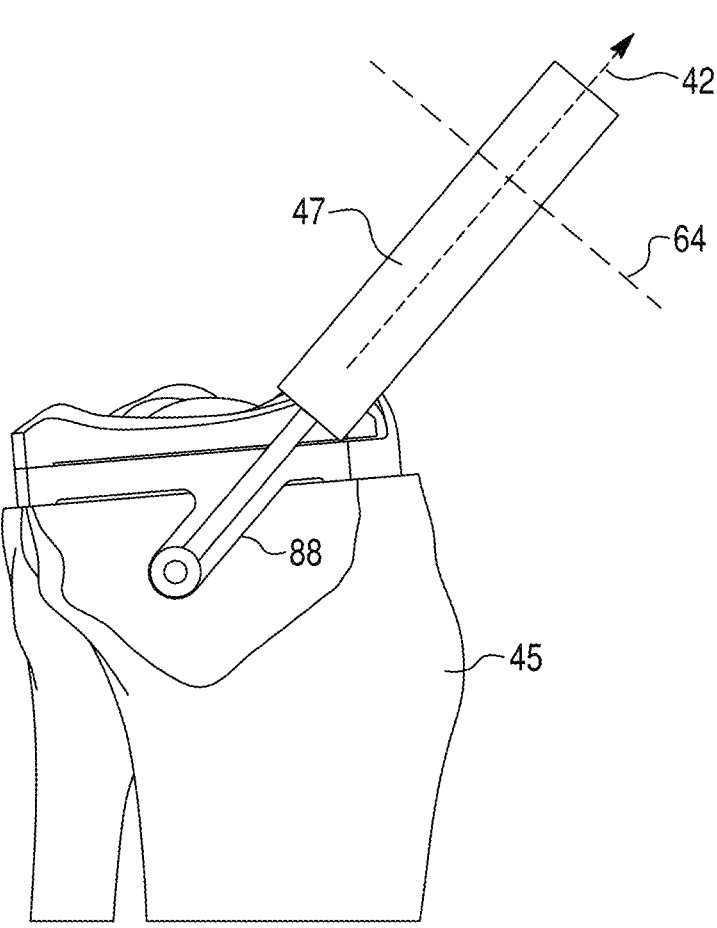
Figure 11E:
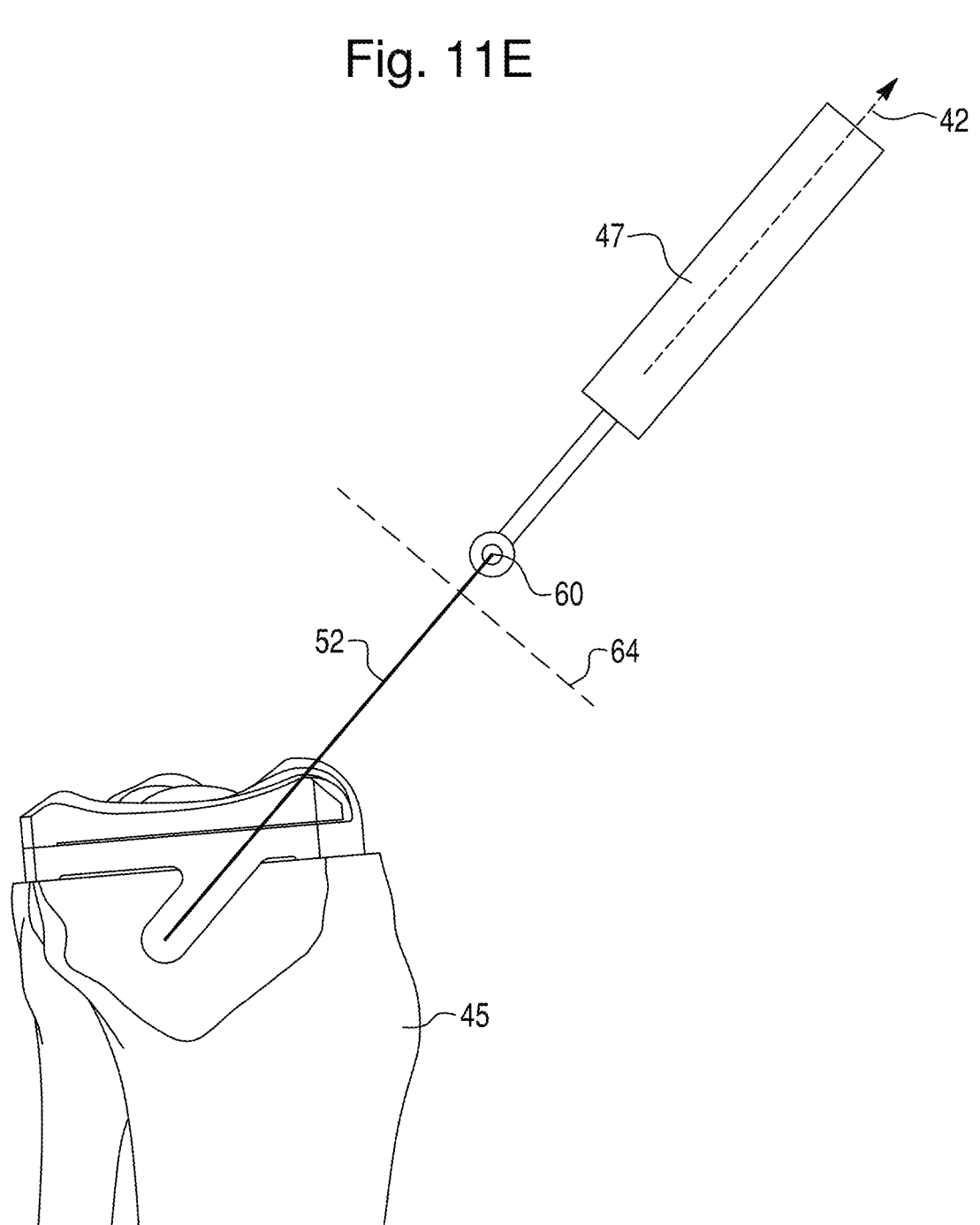
Figure 12:
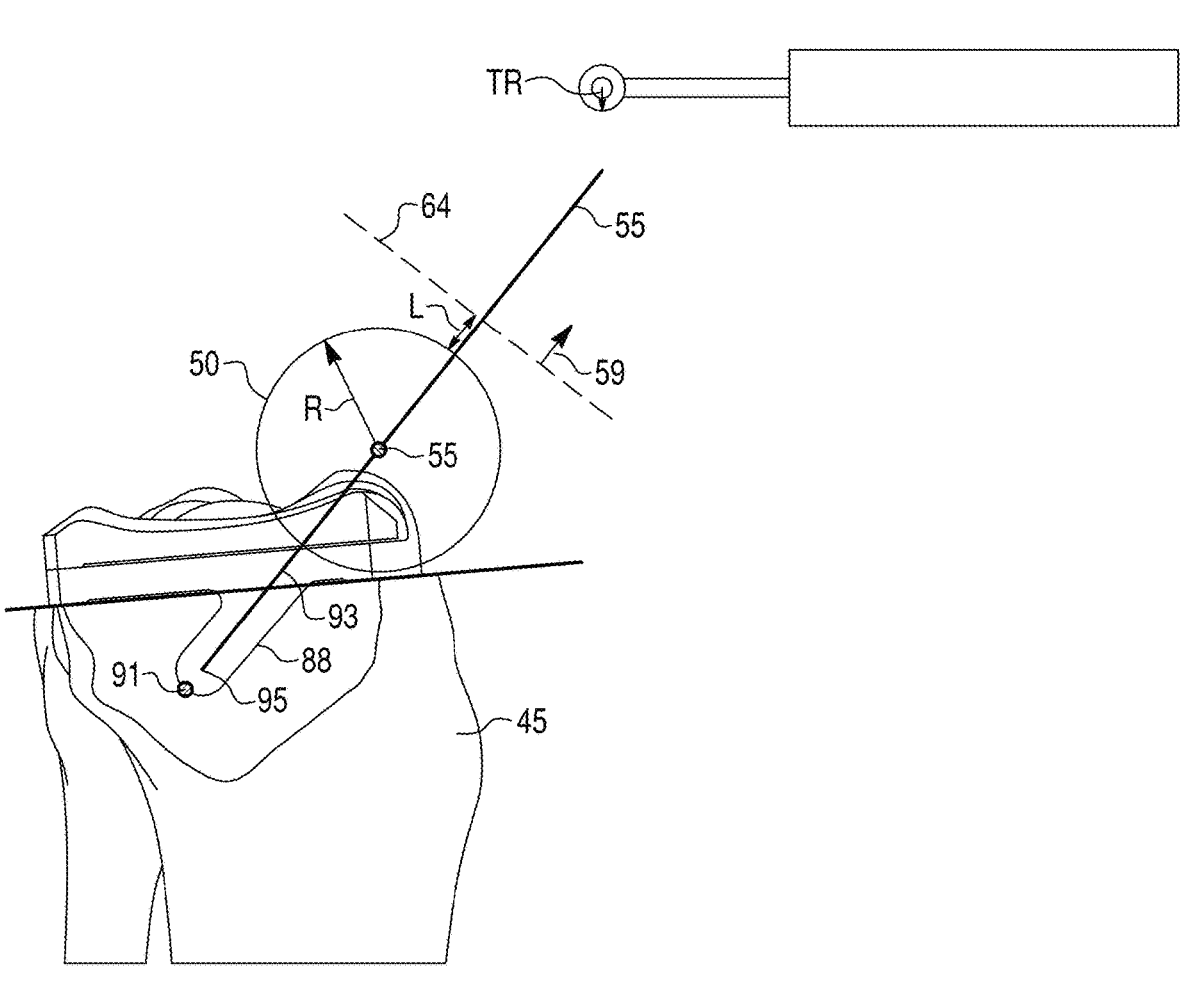
FIG. 12 illustrates various features of the surgical plan of the embodiment of FIGS. 11A-11E.

FIGS. 11A-11E illustrate the virtual environment during another embodiment of entry and exit from haptic control. In this embodiment, the virtual bone model 45 represents a tibia 2. Virtual tool 47 represents a surgical tool 36 in the form of a spherical burr, although the surgical tool 36 can be any tool capable of creating planned hole 88. The planned modification is a hole 88 to receive the peg of a tibial component. The spherical burr can also be used to create holes for receiving pegs of femoral, patellofemoral, or any other type of implant component. In FIGS. 11A-11E, a virtual tibial component 90 is superimposed on the bone model 45 to more clearly illustrate the planned bone modifications. In this embodiment, haptic object 52 is a line. The placement of linear haptic object 52 may be planned based on the dimensions or effective dimensions of surgical tool 36, such as the radius TR of a spherical burr (FIG. 12). For example, a space equivalent to radius TR may be left between the end 95 of haptic object 52 and the bottom of peg tip point 91, as illustrated in FIG. 12.

FIG. 11A illustrates the virtual environment when haptic device 30 is in free mode. At the start of a surgical procedure, the surgeon moves surgical device 36 (FIG. 1) towards the patient until HIP 60 crosses entry boundary 50 (FIG. 11B). In this embodiment, entry boundary 50 is a sphere having a radius R (FIG. 12) and having a target point 55 at its center. Once HIP 60 crosses entry boundary 50, the surgical system automatically aligns surgical tool 36. In one embodiment, the surgical system 100 calculates the shortest distance from HIP 60 to target point 55 and then repositions HIP 60 onto target point 55. The surgical system 100 may also reorient surgical tool 36 such that tool axis 42 is parallel to haptic object 52 (FIG. 11C). HIP 60 is then constrained to movement along linear haptic object 52, and the surgeon can move surgical tool 36 along a linear working boundary corresponding to haptic device 52 to create hole 88 (FIG. 11D).

As in previous embodiments, the exit boundary 64 is activated during portions of haptic control. When the surgeon desires to release haptic control, the surgical tool 36 can be moved until HIP 60 crosses exit boundary 64 (FIG. 11E). Haptic object 52 is then deactivated, releasing haptic control and causing the haptic device 30 to reenter free mode. As discussed in relation to other embodiments, the surgical system 100 may continuously calculate the distance between HIP 60 and exit boundary 64, releasing haptic control when this distance becomes positive. Also as described in connection with previous embodiments, entry boundary 50 can be reactivated after release of haptic control. The surgeon can then reenter haptic control by manipulating surgical tool 36 such that HIP 60 crosses entry boundary 50.

FIG. 12 illustrates additional features of a surgical plan having a linear haptic object 52, such as the surgical plan of FIGS. 11A-11E. The peg axis is a line from peg tip point 91, located on the tip of planned hole 88, to target point 55. Linear haptic object 52 may be a line on the peg axis having a first endpoint at end 95 and a second endpoint located past the target point 55 along the exit normal 59. For example, the second endpoint of haptic object 52 may located 50 mm past the target point 55 in the direction of exit normal 59.

The exit boundary 64 may be planar, located a distance L from the entry boundary 50, and have an exit normal 59 defined as the vector direction from the peg tip point 91 to the target point 55.

Figure 13B:
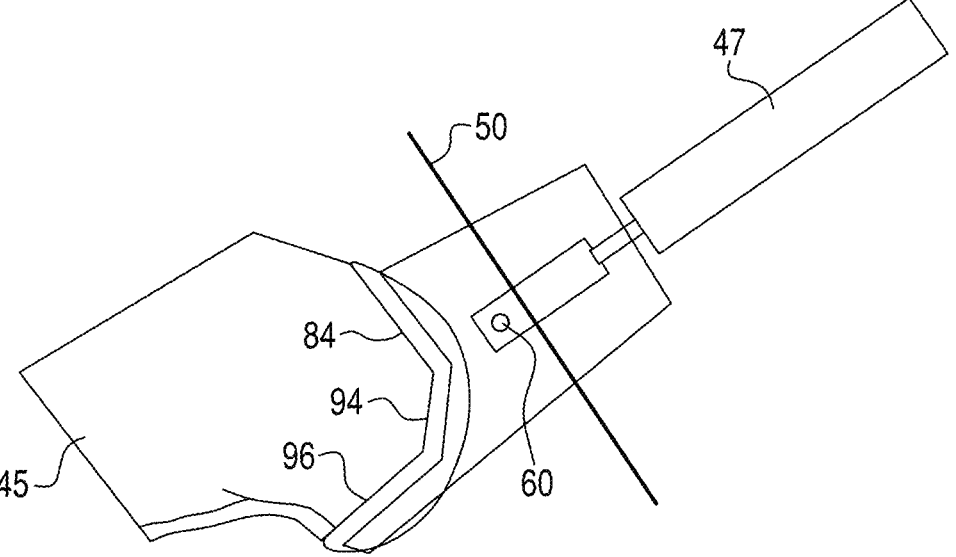
Figure 13C:
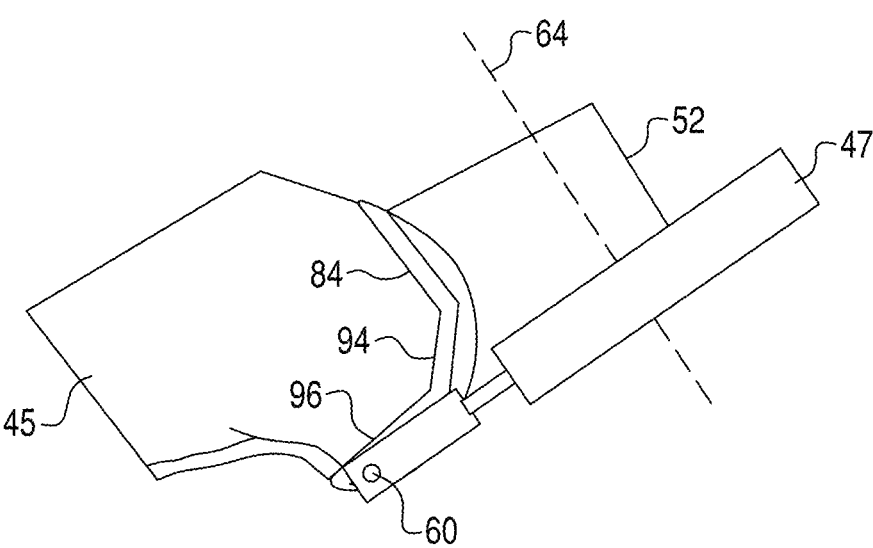
Figure 13D:
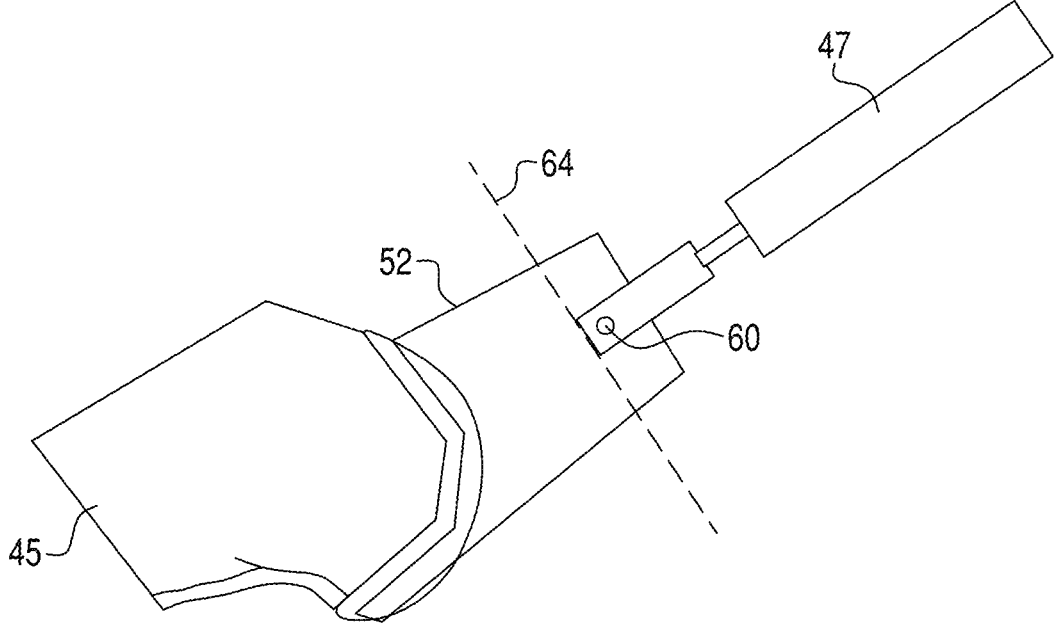

FIGS. 13A-13D illustrate another embodiment of entry into and exit from haptic control. In this embodiment, haptic object 52 is a three-dimensional volume. Virtual bone model 45 can represent any bone 44, such as a femur 4, and virtual tool 47 can represent any type of surgical tool 36 for performing any type of bone modifications. In the virtual environment of FIG. 13A, haptic device 30 is in free mode. To enter haptic control, the user manipulates surgical tool 36 towards the patient's anatomy. Virtual tool 47, including HIP 60, move in correspondence towards entry boundary 50. In this embodiment, entry boundary 50 is a plane that includes target point 55 (not shown). If HIP 60 is within haptic object 52 and HIP 60 crosses entry boundary 50, as shown in FIG. 13B, haptic control is engaged. In haptic control mode, HIP 60 is prevented from exiting the confines of the three-dimensional volume defined by haptic object 52. Further, engagement of haptic control triggers deactivation of entry boundary 50 and activation of exit boundary 64 (FIG. 13C).

The embodiment of FIGS. 13A-13D does not include automatic alignment. In other words, neither the position nor the orientation of surgical tool 36 is modified during haptic control. Consequently, HIP 60 can be freely moved to any position within haptic object 52, and the orientation of surgical tool 36 is not constrained by a haptic object. During haptic control, the surgeon can freely move surgical tool 36 within the working volume corresponding to haptic object 52 to perform the necessary bone modifications, such as cuts corresponding to planned distal cut 84, planned posterior chamfer cut 92, and planned posterior cut 96. FIG. 13C illustrates virtual tool 47 as the surgeon is creating a cut corresponding to planned posterior cut 96. During haptic control in the embodiment of FIGS. 13A-13D, as in previous embodiments, when HIP 60 crosses exit boundary 64 (FIG. 13D), haptic control is released and the haptic device 30 enters free mode. In alternative embodiments, the virtual environment depicted in FIGS. 13A-13D includes additional mechanisms to control the position of HIP 60. For example, planar haptic objects along planned cuts 84, 94, and 96 could constrain HIP 60 to movement along these planar haptic objects. The virtual environment might also include mechanisms to control the orientation of virtual tool 47 (and therefore, of surgical tool 36), such as additional planar or linear haptic objects on which HIP 60 can be constrained.

Figure 14:
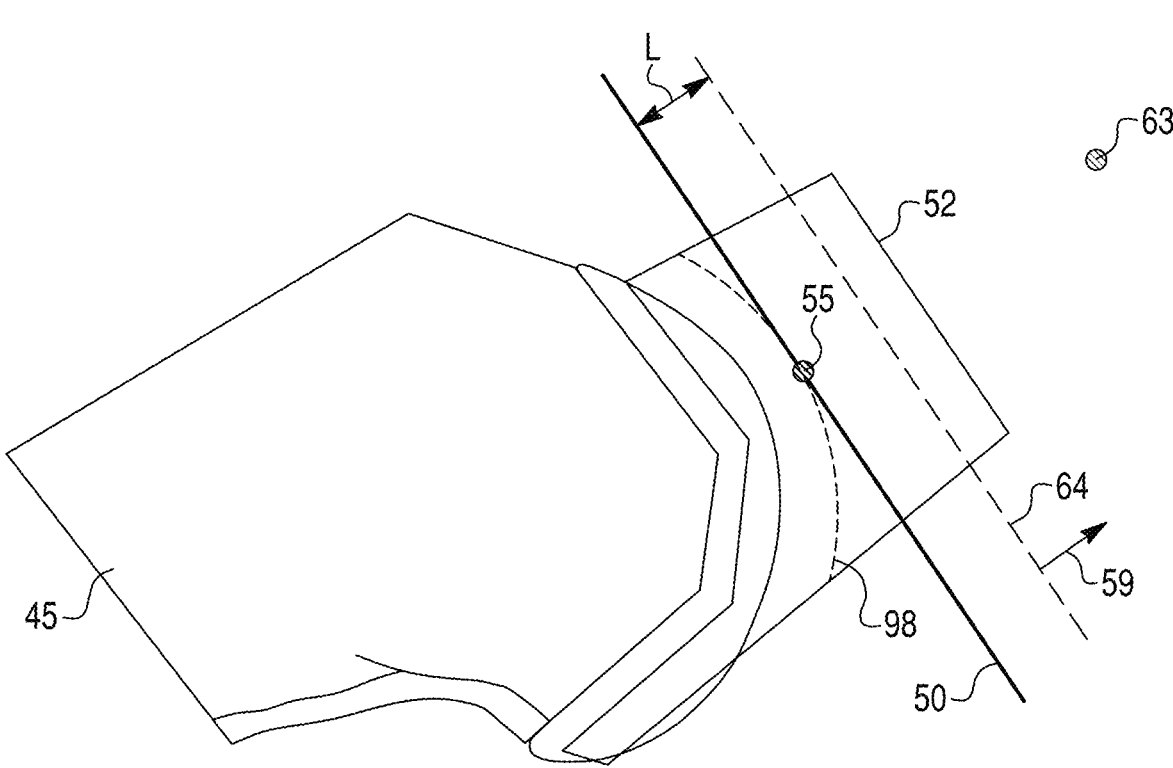
FIG. 14 illustrates various features of the surgical plan of the embodiment of FIGS. 13A-13D.

FIG. 14 illustrates the surgical plan of FIGS. 13A-13D. Exit boundary 64 is parallel to entry boundary 50 and is located a distance L from entry boundary 50 in the direction of exit normal 59. Exit normal 59 is the vector direction from target point 55 to exit normal point 63. FIG. 14 further includes a prior art haptic object 98. In a prior art method of haptic control, a user could not cause an HIP to exit haptic object 98 without performing a separate action to disengage haptic control, such as a pressing a button on input device 22 (FIG. 1). In contrast to prior art haptic object 98, the volumetric haptic object 52 extends farther from the planned cutting surface. Further, the surgical plan associated with haptic object 52 includes an entry boundary 50 and an exit boundary 64. In the presently disclosed embodiments, when the surgeon pulls surgical tool 36 away from the patient and causes HIP 60 to cross exit boundary 64, the surgical system 100 automatically deactivates haptic object 52 to release haptic control. The provision of an exit boundary 64 therefore allows the surgeon greater freedom to release haptic control during surgery. In addition, the interaction between activation and deactivation of the entry boundary 50 and exit boundary 64 described herein allows the surgeon to seamlessly and intuitively enter and exit haptic control by manipulating surgical tool 36, without having to perform separate actions to trigger entry into and exit from haptic control.

Figure 15:
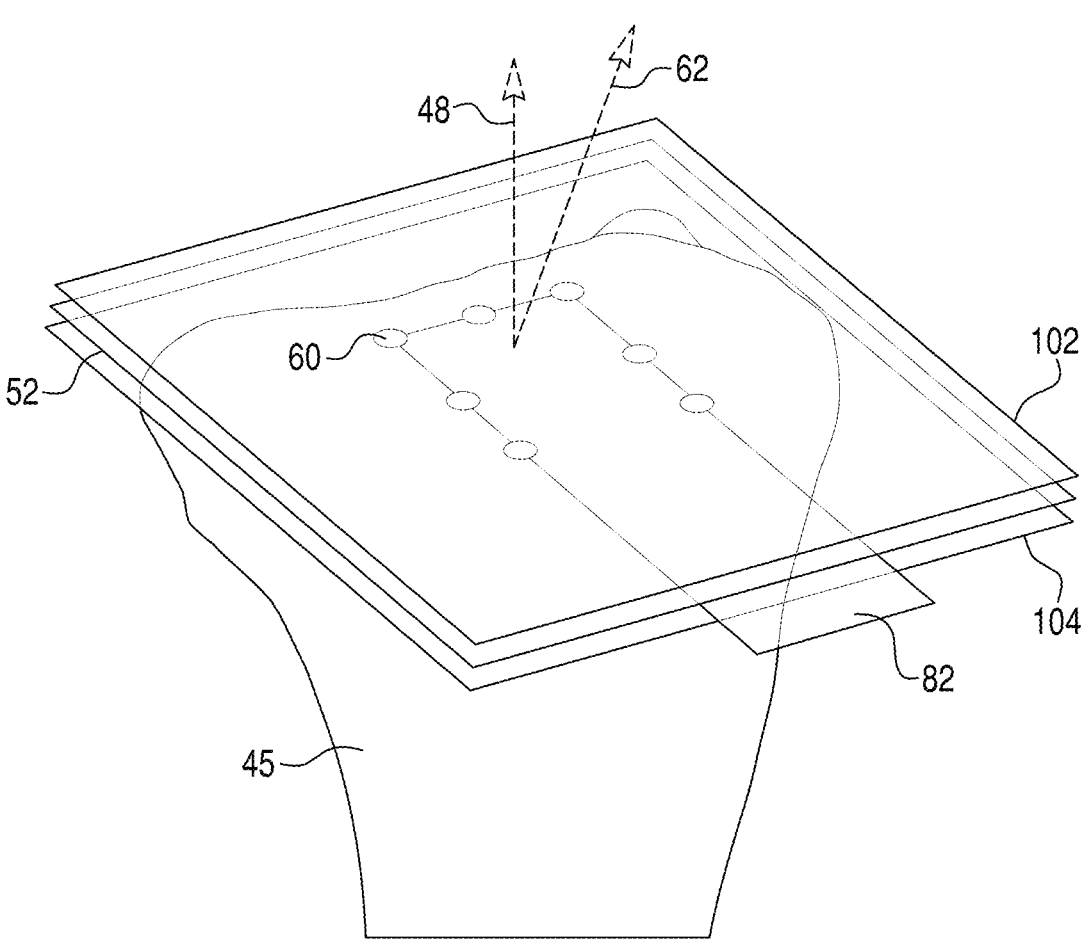
FIG. 15 illustrates a haptic restoration feature employed when haptic control is disengaged.

FIG. 15 illustrates a haptic restoration feature that may be employed in any of the haptic control embodiments described herein. The haptic restoration feature is applicable when haptic control is disengaged for a reason other than because HIP 60 has crossed the exit boundary. Disengagement of haptic control might occur for various reasons, one of which relates to a temporary inability of the navigation system 10 to detect the pose of one or more tracked objects. For example, some navigation systems require a clear path between a detection device 12 and the trackable elements, such as navigation markers 14 and 16, haptic device marker 18, and end effector marker 19 (FIG. 1). If one of the trackable elements is temporarily blocked (i.e. occluded), the navigation system 10 may not be able to effectively determine the pose of one or more tracked objects. As a safety precaution, when a trackable element becomes occluded during a surgical procedure, the surgical system 100 may disengage haptic control of the surgical tool 36. Haptic control may also be disengaged due to sudden movement of a tracked object. For example, the patient's leg or the robotic arm 34 may be bumped, and the navigation system 10 is unable to accurately track the suddenly-moved object. The surgical system will therefore disengage haptic control of the surgical tool 36. Disengagement of haptic control causes the haptic device 30 to enter free mode. The haptic restoration feature can then be utilized to either reengage haptic control by reactivating haptic object 52 or to retain the haptic device 30 in free mode and require the surgeon to reenter entry boundary 50.

To determine whether to reengage haptic control or whether to retain the haptic device 30 in free mode, the surgical system 100 is programmed to evaluate whether various conditions are met after the occlusion, sudden movement, or other factor has caused disengagement of haptic control. In general, the conditions may relate to the position or orientation of a surgical tool 36 relative to the desired, constrained position or orientation of surgical tool 36, and the conditions may depend on the type of surgical tool 36 and the configuration of haptic object 52. Three possible conditions to evaluate may be the tool's orientation, vertical penetration in a haptic plane, and whether all HIPs are within the haptic boundaries. For example, the embodiment of FIG. 15 includes a virtual blade 82, which represents a sagittal saw and includes multiple HIPs (as indicated above, although only one HIP 60 is labeled, references to HIP 60 include references to multiple HIPs). FIG. 15 also includes a planar haptic object 52. In this embodiment, the haptic restoration feature may include determining the orientation of virtual blade 82 relative to haptic object 52 by calculating the angle between tool normal 48 and haptic object normal 62. Tool normal 48 and haptic object normal 62 are ideally parallel if the surgical tool 36 is being constrained during cutting to lie within the working boundary corresponding to planar haptic object 52. One condition may be, for example, whether tool normal 48 and haptic object normal 62 are within two degrees of each other. The surgical system 100 can be programmed to conclude that if this condition is met, the orientation of surgical tool 36 remains substantially accurate even after the temporary occlusion of a trackable element or sudden movement of the patient or robotic arm.

The surgical system 100 may also evaluate the position of HIP 60 relative to planar haptic object 52 (e.g., vertical penetration). FIG. 15 illustrates virtual boundaries 102, 104 above and below haptic object 52. Virtual boundaries 102, 104, can be planned to lie, for example, approximately 0.5 mm away from haptic object 52. A second condition may be whether HIP 60 lies between these virtual boundaries 102, 104. As another example, a third condition may be whether each of the HIPs 60 of virtual blade 82 lie within the outer bounds of haptic object 52.

If each of the relevant conditions are met, the haptic restoration feature reactivates haptic object 52, which reengages haptic control and allows the surgeon to continue cutting. However, if any of the conditions are not met, the haptic device 30 remains in free mode. The surgeon must then cause HIP 60 to cross back into an entry boundary 50 (not shown in FIG. 15), as described in the various embodiments herein. Once HIP 60 crosses entry boundary 50, haptic control can be reengaged. In the embodiment illustrated in FIG. 15, haptic control after HIP 60 has crossed entry boundary 50 may include automatic alignment and subsequent constraint of HIP 60 on planar haptic object 52. In other embodiments, such as the embodiment of FIGS. 13A-13D, haptic control after HIP 60 crosses entry boundary 50 may not include automatic alignment.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although a specific order of method steps may be described, the order of the steps may differ from what is described. Also, two or more steps may be performed concurrently or with partial concurrence (e.g. deactivation of entry boundary 50 and activation of exit boundary 64). Such variation will depend on the software and hardware systems chosen and on designer choice. All such variations are within the scope of the disclosure. Likewise, software implementations could be accomplished with standard programming techniques with rule based logic and other logic to accomplish any connection steps, processing steps, comparison steps, and decision steps.

What is claimed is:

1. A surgical method, comprising:

Operating a surgical robot in a first mode;

Detecting, by a computer, a crossing of an object from a first side of a boundary to a second side of the boundary;

Automatically switching, by the computer in response to the crossing of the object from the first side of the boundary to the second side of the boundary, the surgical robot from the first mode to a second mode; and Operating the surgical robot in the second mode.

2. The surgical method of claim 1, wherein the boundary is correlated with a surgical field.

3. The surgical method of claim 1, wherein operating the surgical robot in the second mode comprises providing automated movement of the surgical robot.

4. The surgical method of claim 3, further comprising stopping the automated movement in response to a sensed movement of a surgeon's hand.

5. The surgical method of claim 1, wherein: operating the surgical robot in the first mode comprises providing automated movement of the surgical robot; and operating the surgical robot in the second mode comprises enabling, by the surgical robot, manual movement of the surgical robot.

6. The surgical method of claim 5, wherein enabling, by the surgical robot, the manual movement of the surgical robot further comprises constraining the manual movement of the surgical robot with a haptic object.

7. The surgical method of claim 1, further comprising switching the surgical robot from the second mode to a third mode in response to the object entering a defined volume.

8. The surgical method of claim 1, wherein the boundary is curved.

9. The surgical method of claim 1, wherein the object is a surgical tool coupled to the surgical robot or a portion of the surgical robot.

10. The surgical method of claim 1, further comprising changing the operating of the surgical robot in the first mode or the second mode based on a sensed position of a hand of a surgeon.

11. The surgical method of claim 1, comprising tracking the object to determine the crossing using data from an optical tracking system.

12. The surgical method of claim 1, comprising tracking the object to determine the crossing using data from joints of the surgical robot.

13. A surgical system, comprising:

a surgical robot; and a controller comprising a processor and non-transitory computer-readable memory storing instructions that, when executed, cause the processor to perform operations comprising:

operating the surgical robot in a first mode;

determining a crossing of an object from a first side of a boundary to a second side of the boundary;

switching, in response to the crossing of the object from the first side of the boundary to the second side of the boundary, the surgical robot from the first mode to a second mode; and operating the surgical robot in the second mode.

14. The surgical system of claim 13, wherein the boundary is correlated with a surgical field.

15. The surgical system of claim 13, wherein operating the surgical robot in the second mode comprises causing automated movement of the surgical robot.

16. The surgical system of claim 15, comprising a sensor configured to detect presence of a hand, wherein the operations further comprise stopping the automated movement based on data from the sensor.

17. The surgical system of claim 13, wherein the second mode is a haptic mode.

18. The surgical system of claim 13, comprising the object, wherein the object is a surgical tool coupled to the surgical robot.

19. The surgical system of claim 13, comprising an optical tracking system configured to provide tracking data, wherein determining the crossing of the object from the first side of the boundary to the second side of the boundary uses the tracking data.

20. The surgical system of claim 13, wherein:

operating the surgical robot in the first mode comprises providing automated movement of the surgical robot; and operating the surgical robot the second mode comprises enabling, by the surgical robot, manual movement of the surgical robot.

\* \* \* \* \*